(12) United States Patent
King

(10) Patent No.: US 11,426,133 B2
(45) Date of Patent: Aug. 30, 2022

(54) EXTERNALLY PLACED ELECTROMAGNETIC FIDUCIAL ELEMENT

(71) Applicant: Lucent Medical Systems, Inc., Kirkland, WA (US)

(72) Inventor: Curtis S. King, Kirkland, WA (US)

(73) Assignee: Lucent Medical Systems, Inc., Kirkland, WA (US)

( * ) Notice: Subject to any disclaimer, the term of this patent is extended or adjusted under 35 U.S.C. 154(b) by 579 days.

(21) Appl. No.: 16/352,778

(22) Filed: Mar. 13, 2019

(65) Prior Publication Data

US 2019/0282188 A1 Sep. 19, 2019

Related U.S. Application Data

(60) Provisional application No. 62/642,513, filed on Mar. 13, 2018.

(51) Int. Cl.
*A61B 6/00* (2006.01)
*A61B 6/12* (2006.01)
(Continued)

(52) U.S. Cl.
CPC ............... *A61B 6/12* (2013.01); *A61B 5/062* (2013.01); *A61B 6/487* (2013.01); *A61B 90/39* (2016.02);
(Continued)

(58) Field of Classification Search
CPC ........... A61B 6/12; A61B 90/39; A61B 6/487; A61B 5/062; A61B 6/032;
(Continued)

(56) References Cited

U.S. PATENT DOCUMENTS 5,425,367 A 6/1995 Shapiro et al.
5,425,382 A 6/1995 Golden et al.
(Continued)

FOREIGN PATENT DOCUMENTS

WO 2017/127722 A1 7/2017

OTHER PUBLICATIONS

Amphenol® RF, "Frequency Range Chart," archived Nov. 9, 2015, URL=https://web.archive.org/web/20151109154937/http://www.amphenolrf.com/frequency-range-chart/, download date Mar. 15, 2017, 3 pages.
(Continued)

*Primary Examiner* — Joel Lamprecht
(74) *Attorney, Agent, or Firm* — Seed IP Law Group LLP

(57) ABSTRACT

Some medical procedures may be assisted by an electromagnetic fiducial element assembly that is affixed to the body of a patient. The electromagnetic fiducial element assembly has a flexible substrate and an affixation mechanism such as an adhesive arranged to removably affix the electromagnetic fiducial element assembly to the body of a patient. The assembly also includes a housing coupled to the flexible substrate that partially or fully contains a first trackable electromagnetic element. A medically imagable structure is integrated with the electromagnetic fiducial element assembly. In the medical procedures, a medical image of a portion of the patient's body is captured, and a representation of the medically imagable structure is visually apparent in the medical image. When a medical device having a second trackable electromagnetic element is advanced into the body of the patient, the medical device, the first and second trackable electromagnetic elements are tracked with a sensor device and an image representing the medical device is formed in the captured medical image.

13 Claims, 16 Drawing Sheets

(51) Int. Cl.
  *A61B 90/00* (2016.01)
  *A61B 5/06* (2006.01)
  *A61B 6/03* (2006.01)
(52) U.S. Cl.
  CPC ....... *A61B 6/032* (2013.01); *A61B 2090/3966* (2016.02); *A61B 2090/3991* (2016.02)
(58) Field of Classification Search
  CPC .... A61B 2090/3966; A61B 2090/3991; A61B 2090/397; A61B 5/4836
  See application file for complete search history.

(56) References Cited

U.S. PATENT DOCUMENTS

| | | | |
|---|---|---|---|
| 5,622,169 | A | 4/1997 | Golden et al. |
| 5,645,065 | A | 7/1997 | Shapiro et al. |
| 5,767,669 | A | 6/1998 | Hansen et al. |
| 5,775,322 | A | 7/1998 | Silverstein et al. |
| 5,879,297 | A | 3/1999 | Haynor et al. |
| 5,902,238 | A | 5/1999 | Golden et al. |
| 6,129,668 | A | 10/2000 | Haynor et al. |
| 6,173,715 | B1 | 1/2001 | Sinanan et al. |
| 6,216,028 | B1 | 4/2001 | Haynor et al. |
| 6,263,230 | B1 | 7/2001 | Haynor et al. |
| 6,292,680 | B1 | 9/2001 | Somogyi et al. |
| 7,158,754 | B2 | 1/2007 | Anderson |
| 7,976,518 | B2 | 7/2011 | Shaughnessy et al. |
| 8,197,494 | B2 | 6/2012 | Jaggi et al. |
| 8,265,732 | B2 | 9/2012 | Besz et al. |
| 8,478,382 | B2 | 7/2013 | Burnside et al. |
| 8,606,347 | B2 | 12/2013 | Besz et al. |
| 8,644,907 | B2 | 2/2014 | Hartmann et al. |
| 8,781,555 | B2 | 7/2014 | Burnside et al. |
| 8,934,960 | B2 | 1/2015 | Besz et al. |
| 9,028,441 | B2 | 5/2015 | Kuhn |
| 9,131,956 | B2 | 9/2015 | Shaughnessy et al. |
| 9,579,488 | B2 | 2/2017 | Shaughnessy et al. |
| 9,585,599 | B2 | 3/2017 | Besz et al. |
| 9,687,174 | B2 | 6/2017 | Jaggi et al. |
| 10,617,324 | B2 * | 4/2020 | Hunter ................. A61B 10/04 |
| 2002/0165448 | A1 | 11/2002 | Ben-Haim et al. |
| 2003/0006759 | A1 | 1/2003 | Govari |
| 2004/0087877 | A1 | 5/2004 | Besz et al. |
| 2008/0004663 | A1 | 1/2008 | Jorgenson |
| 2009/0171190 | A1 | 7/2009 | Uchiyama et al. |
| 2012/0130228 | A1 | 5/2012 | Zellers et al. |
| 2012/0130229 | A1 | 5/2012 | Zellers et al. |
| 2014/0051983 | A1 | 2/2014 | Schroeder et al. |
| 2014/0196723 | A1 | 7/2014 | Kirkpatrick et al. |
| 2015/0238388 | A1 | 8/2015 | Kuhn |
| 2016/0067148 | A1 | 3/2016 | Nordquist et al. |
| 2017/0128701 | A1 | 5/2017 | Shaughnessy et al. |
| 2017/0143235 | A1 | 5/2017 | Besz et al. |

OTHER PUBLICATIONS

International Search Report, dated Apr. 7, 2017, for International Application No. PCT/US2017/014395, 2 pages.

Sacolick et al., "Electromagnetically tracked placement of a peripherally inserted central catheter," *SPIE Medical Imaging Proceedings*, 2004, 5 pages.

* cited by examiner

EXTERNALLY PLACED ELECTROMAGNETIC FIDUCIAL ELEMENT

BACKGROUND

Technical Field

The present disclosure generally relates medical imagery used to track access to a selected location in the body of a patient. More particularly, but not exclusively, the present disclosure relates to a structure visible via medical imaging and having a trackable electromagnetic element in the body of a patient.

Description of the Related Art

In many medical procedures, a medical practitioner accesses an internal cavity, structure, or other physiological element of a patient using a medical instrument. In some cases, the medical practitioner accesses the internal locus of interest for diagnostic purposes. In other cases, the practitioner accesses the locus of interest to provide treatment. In still other cases different therapy is provided.

For many reasons, including the sensitivity of internal tissues of a patient's body, incorrectly positioning the medical instrument within the body can cause harm. Accordingly, it is beneficial to be able to precisely track the position of the medical instrument within the patient's body. However, accurately tracking the position of the medical instrument within the body can be quite difficult. The difficulties are amplified when the medical instrument is placed deep within the body of a large patient.

It is known that electromagnetic coil based medical instruments may be tracked as the instrument travels or remains stationary within the patient's body. For example, International Application No. PCT/US2017/014395 to Andreason et al. is entitled, LOW-FREQUENCY ELECTROMAGNETIC TRACKING. Here, systems, devices, and methods to track one or more low-frequency electromagnetic trackable structures are described. Embodiments of such teaching include advancing a medical instrument into the body of a patient, wherein the medical instrument has at least one low-frequency electromagnetic apparatus affixed thereto. The low-frequency electromagnetic apparatus includes at least one ferromagnetic core and at least one conductor, each of which may be dedicated or shared. The at least one conductor has a first portion arranged as a plurality of coils wound around a ferromagnetic core and a second portion arranged as a set of conductive leads. Embodiments of the teaching further include applying a low-frequency excitation signal to the set of conductive leads and detecting in real time, from outside the patient's body, at least one magnetic field produced by the low-frequency electromagnetic apparatus. In some embodiments, visual information is presented to track the motion or stationary position of the medical instrument inside the body of the patient based on the detected magnetic field. International Application No. PCT/US2017/014395 to Andreason et al. is incorporated herein by reference to the fullest extent allowed by law.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

The present disclosure describes embodiments of an externally placed electromagnetic fiducial element and methods of determining the location of a medical device within the body of a patient using an externally placed electromagnetic fiducial element as a reference marker. The electromagnetic fiducial element includes at least one medically imagable structure. The medically imagable structure may, for example, be a cross-hair or other pattern formed with radiopaque material (e.g., gold, titanium, silver, barium sulfate, bismuth, tungsten, or the like) that is visible in medical imaging (e.g., fluoroscopy, x-ray).

The medically imagable structure is affixed to the patient prior to commencing a medical procedure. After the medically imagable structure is affixed to the patient, one or more medical images of the patient are captured. The medical images may be x-ray images, fluoroscopy images, magnetic resonance imaging (MRI) images, computed tomography (CT) scans, ultrasound images, or images from some other type of medical imaging methodology. In the present disclosure, descriptions of embodiments are provided that reference a medical image, a plurality of medical images, or other like terms.

It is recognized that such terms are not limiting, and that in some cases, a medical procedure captures a single medical image, and in other cases, a medical procedure captures a plurality of medical images. One of skill in the art will recognize that wherein a single image is described, a plurality of images may also be used, and where a plurality of images are described, a single image may also be used.

In a preferred embodiment, the medical imaging used will show internal structures of the body, such as bones, and might, in some images, also show internal organs of the patient. After the medical image is obtained, it is stored as a completed image or set of images. For many types of medical scans, such as CT scan, MRI, and the like, a large number of images are captured and stored. The set of images might be organized as a series of images, each at a slightly different location or taken at a slightly different angle of the patient. These stored images might also be organized as a video or other format for easy viewing by the medical practitioner to see one image relative to the other. The completed image or sets of images can then be retrieved and viewed by the medical practitioner at a later time when the live image is no longer being obtained.

In one embodiment, the active real time imaging to create a medical image of the patient is now terminated. The medical image that was obtained is displayed for the medical practitioner to view in the next step of the medical procedure.

The medical procedure proceeds to the next stage by advancing a medical device into the body of the patient. The medical device has an associated trackable electromagnetic element. For example, if the medical device is a medical tube, an electromagnetic coil assembly may be formed on or otherwise integrated with a distal end of the medical tube that is advanced into the body of the patient.

One or more sensors located outside of the patient's body detect electromagnetic signals produced by a plurality of electromagnetic devices that are located inside, outside, or otherwise in proximity of the patient's body. These signals are used to determine the position of the medical device having the trackable electromagnetic element as it is advanced, moved, or otherwise manipulated within the body of the patient.

In addition, from the tracking information, a representation of the medical device is tracked, painted, overlaid, displayed, or otherwise integrated with one or more of the medical images previously captured and stored as the completed image. The completed image is displayed as a static image at a location that can be viewed by a medical practitioner at the same time the medical device is advancing in the patient's body. The patient's body itself is not being imaged as the medical device advances in the body. Instead, the medical device is being tracked by sensors that detect the trackable electromagnetic elements, and the location of the medical device or its associated electromagnetic element is displayed on the static, previously stored medical image of the patient as the medical device advances in the body. In this way, the medical practitioner can observe the previously captured medical images and see the motion of the medical device in real time being displayed on the previously stored medical images. The medical device will appear to be moving as a displayed element that is overlaid or otherwise presented on a still x-ray or other medical image. Alternatively, the motion may appear as the medical device moving in a previously obtained video of the patient's internal structures. For example, a CT scan, MRI, or other complex scan may be stored as a large number of images and might be organized as a video. As the medical device advances from one image to the next of the stored images, the medical device may appear as a moving device from one image to the next in a previously stored video.

If the medical procedure includes two electromagnetic elements (e.g., one on the medically imagable structure affixed to the patient before beginning the medical procedure and one on the medical device), the medical device can be tracked in the previously captured medical image relative to the medically imagable structure affixed to the patient (i.e., relative to a reference device) on the static medical image of the patient. If the medical procedure includes a third or more electromagnetic elements (e.g., a second or more medically imagable structures affixed to the patient before beginning the medical procedure), the medical device can be tracked relative to yet another reference device on the static medical image of the patient. In this way, in addition to tracking a medical device in three dimensional space with five degrees of freedom, the sensor device is further arranged to use a reference coil of the medically imagable structure affixed to the patient and visible in the two- or three-dimensional (2D or 3D) medical image data as a means to register the coordinate system of the sensor to the coordinate system of the 2D or 3D medical image, and to track multiple stationary, moving, or stationary and moving electromagnets within that space relative to the reference coil or the sensor. In other words, the systems, devices, and methods (i.e., the teaching of the present disclosure) proposed herein permit a determination of the location of the sensor and the location of one or more trackable devices relative to a 2D or 3D medical image that has been previously captured and stored at a prior time.

One embodiment of the electromagnetic fiducial element assembly may be summarized as including a flexible substrate and an affixation mechanism, which may in some cases be integrated with the flexible substrate, arranged to removably affix the electromagnetic fiducial element assembly, via the flexible substrate, to a patient's body. A housing is coupled to the flexible substrate, the housing enclosing or otherwise containing a trackable electromagnetic element. A medically imagable structure arranged to form a visually apparent representation of the medically imagable structure in a medical image of a portion of the patient's body that was previously captured and stored when the electromagnetic fiducial element is affixed to the patient's body.

The medically imagable structure may be formed from a radiopaque material, and the stored medical image may be an x-ray image, CT scan, or a fluoroscopy image. The medically imagable structure may be shaped as a crosshair. The affixation mechanism may be an adhesive. The electromagnetic fiducial element assembly may include a second trackable electromagnetic element.

An electromagnetic fiducial element assisted medical procedure may be summarized as including: affixing an electromagnetic fiducial element to a patient's body, the electromagnetic fiducial element having a first trackable electromagnetic and a medically imagable structure, and in at least some cases, the electromagnetic fiducial element may also include a flexible substrate; and an affixation mechanism arranged to removably affix the electromagnetic fiducial element assembly to the patient's body. The procedure may be further summarized as including: capturing a medical image of a portion of the patient's body, wherein a representation of the medically imagable structure is visually apparent in the medical image; advancing a medical device into the body of the patient, the medical device having associated therewith a second trackable electromagnetic element; tracking the first and second trackable electromagnetic elements with a sensor device arranged to track a plurality of trackable electromagnetic elements; and presenting the medical image of the portion of the patient's body wherein the medically imagable structure is visually apparent in the captured medical image and wherein a representation of at least a portion of the medical device is visually apparent in the captured medical image.

The electromagnetic fiducial element assisted medical procedure may include presenting, in real time, motion of the representation of at least the portion of the medical device in the captured medical image. The procedure may include capturing the medical image with an x-ray procedure, and presenting the medical image of the portion of the patient's body may comprise presenting the representation of at least the portion of the medical device in real time in two dimensions in the of medical image. The electromagnetic fiducial element assisted medical procedure may include capturing a series of medical images with an fluoroscopy procedure, and presenting the medical image of the portion of the patient's body may include presenting the representation of at least the portion of the medical device in real time in three dimensions in the series of medical images.

The electromagnetic fiducial element assembly may include a third trackable electromagnetic element. The affixation mechanism may be an adhesive. Alternatively, or in addition, the affixation mechanism is may be a belt. The electromagnetic fiducial element assisted medical procedure may include supplying a first excitation signal having a first frequency between about 200 Hz and about 500 Hz to the first trackable electromagnetic element; and supplying a second excitation signal having a second frequency between about 200 Hz and about 500 Hz to the second trackable electromagnetic element.

A system may be summarized as including: an electromagnetic fiducial element assembly, the electromagnetic fiducial element assembly having: a flexible substrate; an affixation mechanism arranged to removably affix the electromagnetic fiducial element assembly, via the flexible substrate, to a patient's body; a first trackable electromagnetic element; and a medically imagable structure. The system may further include a medical device having associated therewith a second trackable electromagnetic element; and a sensor device arranged to track a plurality of trackable electromagnetic elements.

The system may further include at least one control circuit arranged to generate an excitation signal having a frequency between about 200 Hz and about 500 Hz; and at least one conduit to pass the excitation signal to at least one of the first and second trackable electromagnetic elements. The system may include a presentation device coupled to the sensor device and arranged to present at least one medical image of a portion of the patient's body wherein the medically imagable structure is visually apparent in the at least one medical image and wherein a representation of at least a portion of the medical device is visually apparent in the at least one medical image. The electromagnetic fiducial element assembly may be a single use disposable device. The electromagnetic fiducial element may be a reusable device.

This Brief Summary has been provided to describe certain concepts in a simplified form that are further described in more detail in the Detailed Description. The Brief Summary does not limit the scope of the claimed subject matter, but rather the words of the claims themselves determine the scope of the claimed subject matter.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Figure 1:
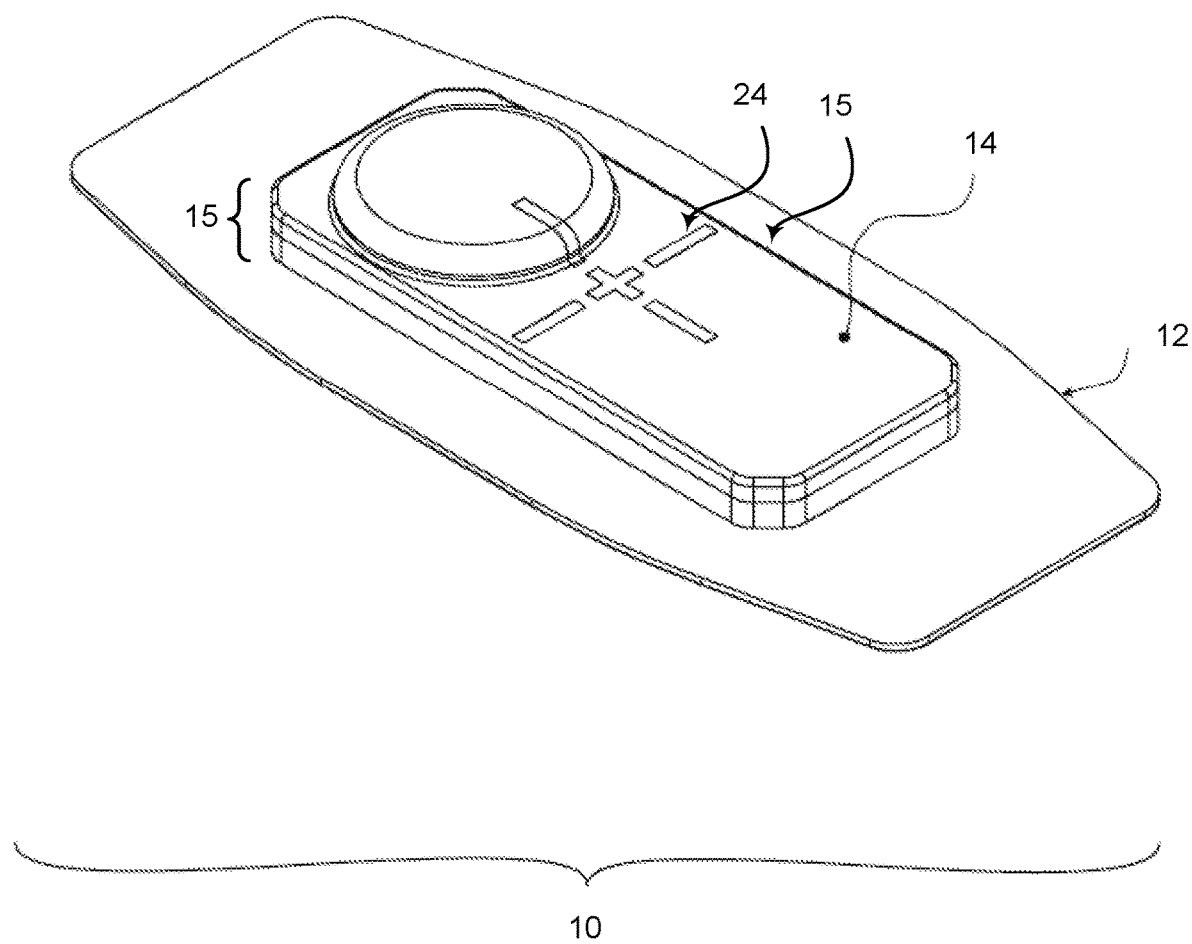
FIG. 1 is an isometric view of an embodiment of an electromagnetic fiducial element assembly according to the disclosure.

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments.

In some medical procedures, a medical practitioner determines that a medical device should be accurately tracked as the device is advanced and otherwise moved inside the body of a patient. In many cases, an imaging modality such as x-ray is used, and in at least some of these cases, fluoroscopy is used to track the medical device as it moves inside the patient's body. The medical practitioner may determine that such modalities expose the patient to an undesirable level of imaging (e.g., an unsafe level of x-rays).

To overcome the limitations of conventional medical device tracking technologies, the present inventor has recognized that an electromagnetic fiducial element assembly may be affixed to a patient, and then one or more medical images of a patient may be captured. The electromagnetic fiducial element assembly has a trackable electromagnetic element and a medically imagable structure. The medically imagable structure will be visually apparent in the captured medical images. Later, a medical device, which also has a trackable electromagnetic element, is advanced into the patient by a medical practitioner. Using a sensor device, the two trackable electromagnetic elements (i.e., one on the medical device and one on the electromagnetic fiducial element assembly that is affixed to the patient) can be concurrently tracked, and a representation of the medical device can be presented in real time on the earlier captured one or more medical images. The medical practitioner can track the medical device to a desired location inside the body of the patient, while the patient avoids over-exposure to x-rays or other medical imaging energy.

The device, method, and system embodiments described in this disclosure (i.e., the teachings of this disclosure) assist in certain medical procedures. The teaching includes an electromagnetic trackable structure, and the trackable structure includes a low-frequency electromagnetic apparatus that is trackable with a magnetic field sensing device. In some cases, a single electromagnetic trackable structure includes a plurality of low-frequency electromagnetic apparatuses. Except where expressly called out, however, in the present disclosure, the terms "electromagnetic trackable structure," "low-frequency electromagnetic apparatus," and other such terms may be used interchangeably and in the singular or plural in any relevant context.

The magnetic field sensing device discussed herein, which may also be called simply a sensor, includes particular algorithms to identify and track the position of one or more low-frequency electromagnetic devices. These one or more low-frequency electromagnetic devices are tracked in three dimensions and the orientation of each device may be tracked relative to one or more other low-frequency electromagnetic devices, to one or more reference points, or to both reference points and other low-frequency electromagnetic devices.

A user interface (e.g., a display, an audio device, a tactile device, etc.) is associated with the magnetic field sensing device. The user interface is arranged to take input information from a medical practitioner and further used to present output information to a medical practitioner. The output information may, for example, represent the position and orientation of at least one of the low-frequency electromagnetic trackable structures. In addition, or in the alternative, the output information may represent the position and orientation of at least one device associated with a low-frequency electromagnetic trackable structure.

FIG. 1 is one embodiment of an electromagnetic fiducial element assembly 10. In some cases, the assembly is a single use disposable device. In some cases, all or a portion of the electromagnetic fiducial element assembly 10 embodiment is reusable. The re-use may include a cleaning, disinfection, sterilization, or some other procedure such as ultraviolet light disinfection, alcohol wipe down, a chemical bath.

The electromagnetic fiducial element assembly 10 of FIG. 1 includes a flexible, bondable strip 12 and an electromagnetic fiducial element 14. The bondable strip 12 may be formed from plastic, rubber, fabric, or any other substrate material. The bondable strip may be rigid, semi-rigid, or even very rigid and still be considered flexible. In some cases, flexible refers to the use of the bondable strip, which may be flexibly located on nearly any desirable portion of a patient's body along the lines of how an adhesive bandage is placed on a patient's body.

The bondable strip 12 includes an affixation mechanism to removably secure the electromagnetic fiducial element assembly. This affixation mechanism, is a bonding means 26 (FIG. 2) such as an adhesive, a tape, a glue, a suture, a staple, a belt, a holster, a clamp, or any other such mechanism that permits removable and relatively secure affixation of the electromagnetic fiducial element assembly 10 embodiment to a patient's body. A relatively secure affixation includes an affixation in which a reasonable medical practitioner will expect the electromagnetic fiducial element assembly 10 to remain affixed on the patient's body with little or no migration for the duration of the medical procedure, including at least some cases, where the medical procedure will last over a period of two or more days.

The electromagnetic fiducial element assembly 10 includes an electromagnetic fiducial element 14 having a medically imagable structure 24. The electromagnetic fiducial element 14 is arranged to include a housing 15 that partially or completely contains (e.g., envelops, encloses, covers, shrouds, surrounds, conceals, or the like) a trackable electromagnetic element.

Figure 2:
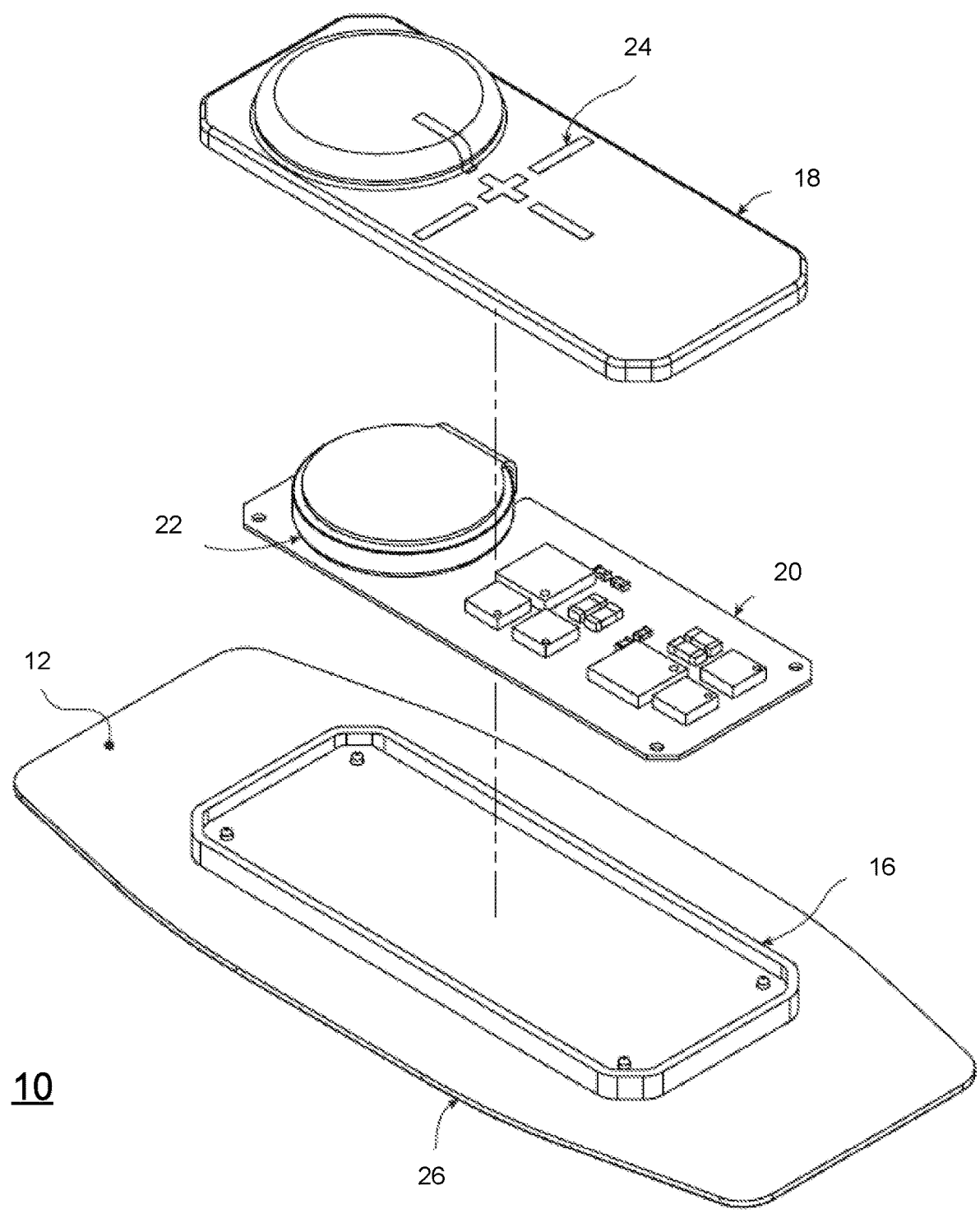
FIG. 2 is an exploded view of the electromagnetic fiducial element assembly embodiment of FIG. 1.

FIG. 2 is an exploded view of the electromagnetic fiducial element assembly 10 embodiment of FIG. 1. The electromagnetic fiducial element assembly 10 of FIG. 2 illustrates a housing 15 arranged with an optional bottom shell 16, an optional top shell 18, and a low frequency coil drive printed circuit board (PCB) 20. An optional battery 22 (e.g., a coin cell) and other electronic components are arranged on the PCB 20. The housing partially or fully contains or otherwise contains the PCB 20, and at least in some cases, the housing 15 is arranged to provide electromechanical stability to the electromagnetic fiducial element assembly 10. When in operation, a low frequency signal controllably energizes an electromagnet of the electromagnetic fiducial element assembly 10, and the electromagnet can be tracked during a medical procedure. Hence, it is appreciated that the electromagnet of the electromagnetic fiducial element assembly 10 can be driven in a wired arrangement, a wireless arrangement, a combined wired and wireless arrangement, or some other arrangement.

In the assembly of FIG. 2, the optional top shell 18 of housing 15 includes a medically imagable structure 24. In FIG. 2, the medically imagable structure 24 is arranged as a crosshair. Other arrangements such as a bulls-eye, a coded symbol, an identifier, or any other desirable arrangement may be used. In addition, the medically imagable structure 24 may be arranged on the optional top shell 18 as in FIG. 2. Additionally, or alternatively, the medically imagable structure 24 may be arranged inside of the housing 15 or on any other portion of the electromagnetic fiducial element assembly 10. In a preferred embodiment, the medically imagable structure 24 is arranged such that a representation of the medically imagable structure 24 will be visually apparent in a medical image of a portion of the patient's body when the electromagnetic fiducial element is affixed to the external body of the patient and when the medical image is captured.

In some cases, the medically imagable structure 24 is formed from a radiopaque material such as gold, silver, platinum, tungsten, bismuth, barium-sulfate, or any other suitable substance, compound, or material. Any other suitable material may also be chosen. A representation 25 (FIG. 8) of the medically imagable structure 24 may be readily seen in an x-ray image, in fluoroscopy images, or in some other medical imagining technique (e.g., ultrasound, computed tomography (CT), magnetic resonance imaging (MRI), or the like.

In FIG. 2, a bonding means 26 is on a bottom portion of the electromagnetic fiducial element assembly 10 for affixing the assembly to a object, such as the body of a patient, an article of clothing on the patient, or other item. The bonding means 26 in FIG. 2 may be an adhesive such as that used in ordinary sterile adhesive bandages or any acceptable type for adhering the assembly to the desired object. Other means of bonding the electromagnetic fiducial element assembly 10 embodiment to the patient are contemplated including sutures, staples, clips, clamps, forceps, or the like.

Figure 3A:
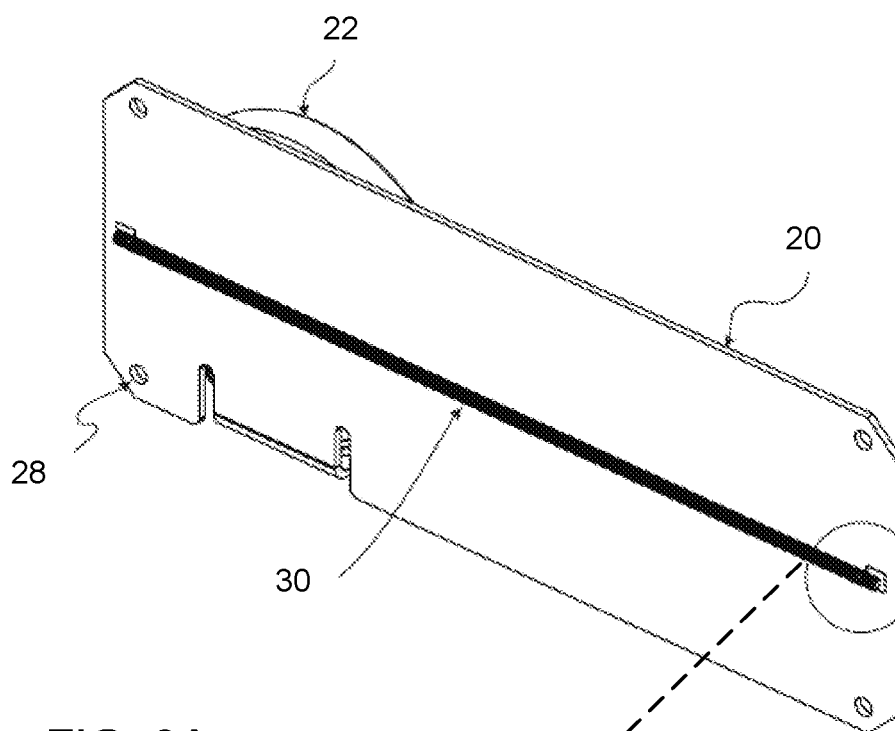
FIG. 3A is an embodiment of an electromagnetic coil assembly.
Figure 3B:
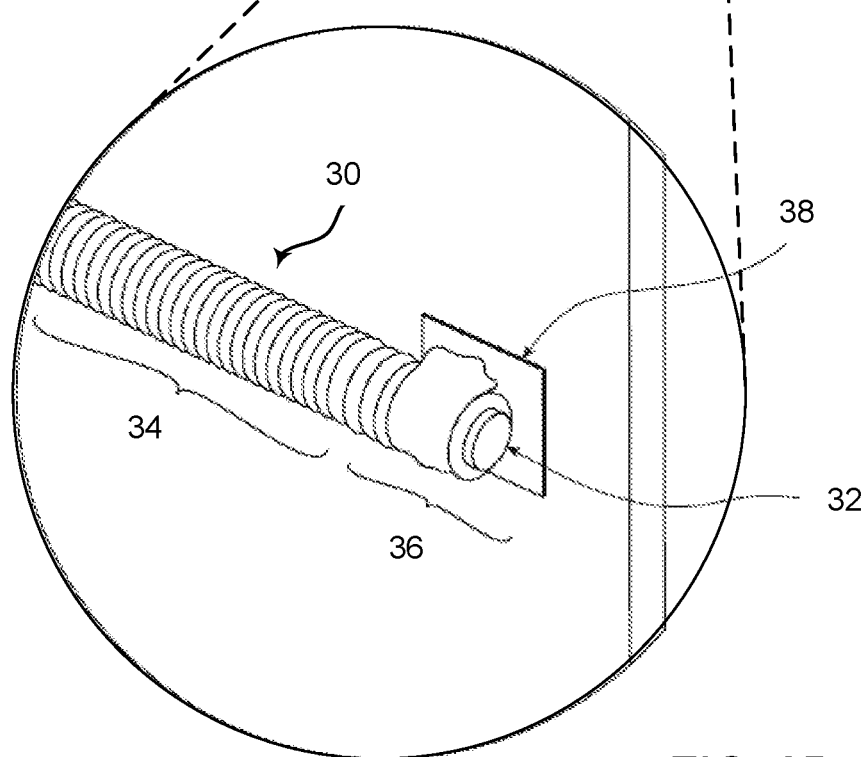
FIG. 3B is an enlargement of a portion of FIG. 3A.

FIG. 3A is an embodiment of an electromagnetic coil assembly 30 of the electromagnetic fiducial element assembly 10 of FIG. 1. FIG. 3B is an enlarged portion of FIG. 3A. In the embodiment of FIG. 3A, the electromagnetic coil assembly 30 is mounted or otherwise integrated with a bottom surface of PCB 20, but other arrangements are contemplated including integrating the electromagnetic coil assembly 30 in a different portion of PCB 20, in a different orientation on PCB 20, separate from PCB 20, or in some other way. An enlarged view taken from FIG. 3A is shown in FIG. 3B to more clearly illustrate an embodiment of the electromagnetic coil assembly 30. For example, the electromagnetic coil assembly 30 is shown as a black strip in FIG. 3A because it has a very dense wiring wrap, but the wrapped coil can be seen more clearly in FIG. 3B, which also shows the electromagnetic coil assembly 30 having a core 20, an electromagnetic coil section 34, and a coil soldering contact section 36 that affixes the wire coil itself to a drive circuit via an electromagnetic coil assembly bond pad contact 38 embodiment. In one embodiment, the electromagnetic coil assembly 30, when energized, provides the electromagnet as discussed elsewhere herein. This embodiment of the electromagnetic coil assembly 30 in FIG. 3A is readily manufacturable by ones of skill in the art, but the disclosure is not limited to simply this implementation. Other configurations of providing an electromagnetic coil assembly 30 in association with an electromagnetic fiducial element assembly 10 are of course contemplated.

The PCB 20 depicted in FIG. 3A includes one or more assembly features such as PCB assembly structure 28 (e.g., holes, protuberances, snap-fit structures, guides, markings, and the like), which in this case is a hole. The PCB assembly structure 28 and other optional assembly features may be used to provide guidance in assembly of a housing (e.g., option top and bottom shells 16, 18), provide electromechanical stability, provide alignment of the electromagnetic coil assembly 30 with a medically imagable structure 24 or some other reference feature, or the like.

Figure 4:
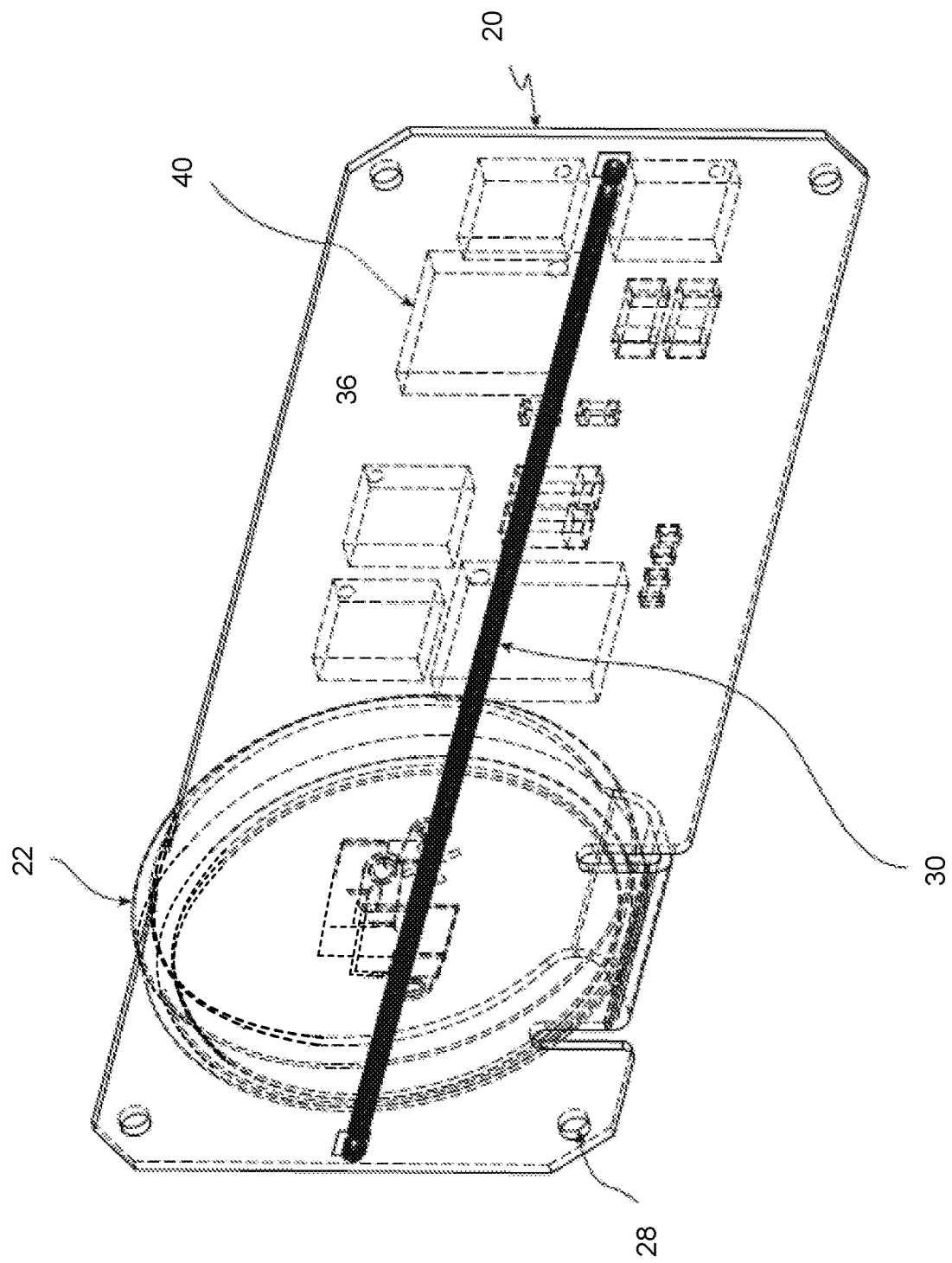
FIG. 4 is a partial hidden line view of a printed circuit board of the electromagnetic fiducial element assembly embodiment of FIG. 1

FIG. 4 is a hidden line view of a printed circuit board (e.g., PCB 20) of the electromagnetic fiducial element assembly 10 embodiment of FIG. 1. The embodiment, which can be efficiently and cost-effectively manufactured, does not expressly limit the structures or features discussed in the present disclosure. Instead, many other formations of electromagnetic coil assemblies (e.g., electromagnetic coil assembly 30), drive circuits, electronics, power sources (e.g., battery 22), mounting substrates (e.g., PCB 20), assembly assistance structures (e.g., PCB assembly structure 28) shapes, dimensions, and the like have been considered by the inventors. The presented subject matter of FIG. 4 and other figures in the disclosure are selected to more clearly convey the inventive content to those of ordinary skill in the art without obscuring the relevant and the optional features.

In FIG. 4, a controller 40 is among the other electronics arranged on PCB 20. The controller 40 may be arranged as a processor having on-board memory or access to off-board memory that stores instructions that are executable by the controller 40. Alternatively, the controller 40 may be arranged as a hardware-based state machine or some other logic. The controller 40 may be used to direct signals passed to the electromagnetic coil assembly 30 to desirably create a trackable magnetic field.

Figure 5:
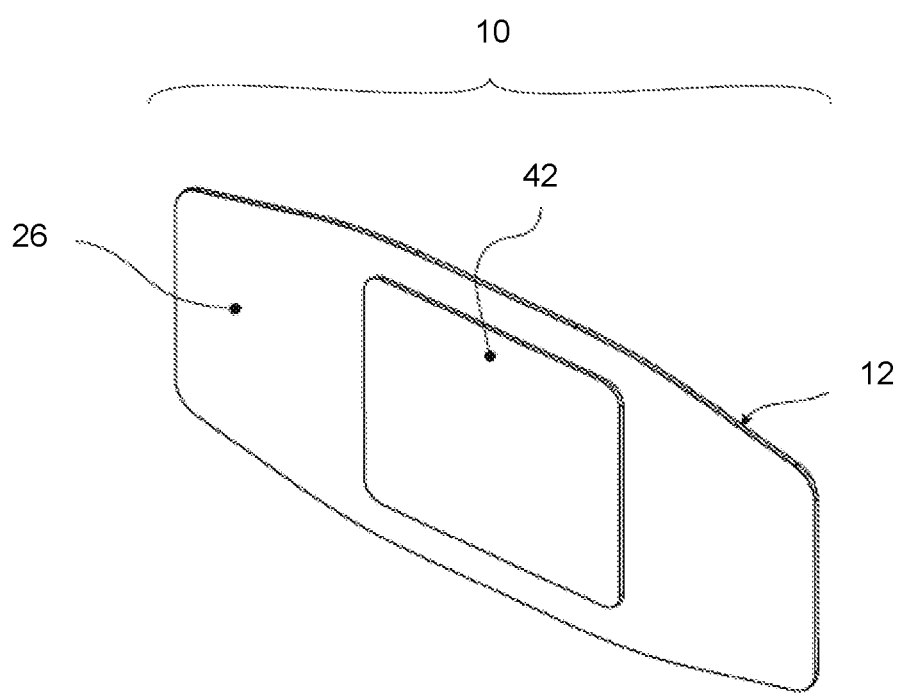
FIG. 5 is a bottom view of the electromagnetic fiducial element assembly embodiment of FIG. 1.

FIG. 5 is a bottom view of the electromagnetic fiducial element assembly 10 embodiment of FIG. 1. The bondable strip 12 has the bonding means 26 on one surface, which may include an adhesive or other bonding means as discussed herein, for removably affixing the electromagnetic fiducial element assembly 10 to an external location of a patient's body. In the embodiment of FIG. 5, the electromagnetic fiducial element assembly 10 includes a non-bonding region 42 of the electromagnetic fiducial element assembly 10 that is in proximity to the electromagnetic fiducial element 14. Namely, in this embodiment, the region 42 does not have any adhesive or other bonding means.

Figure 6:
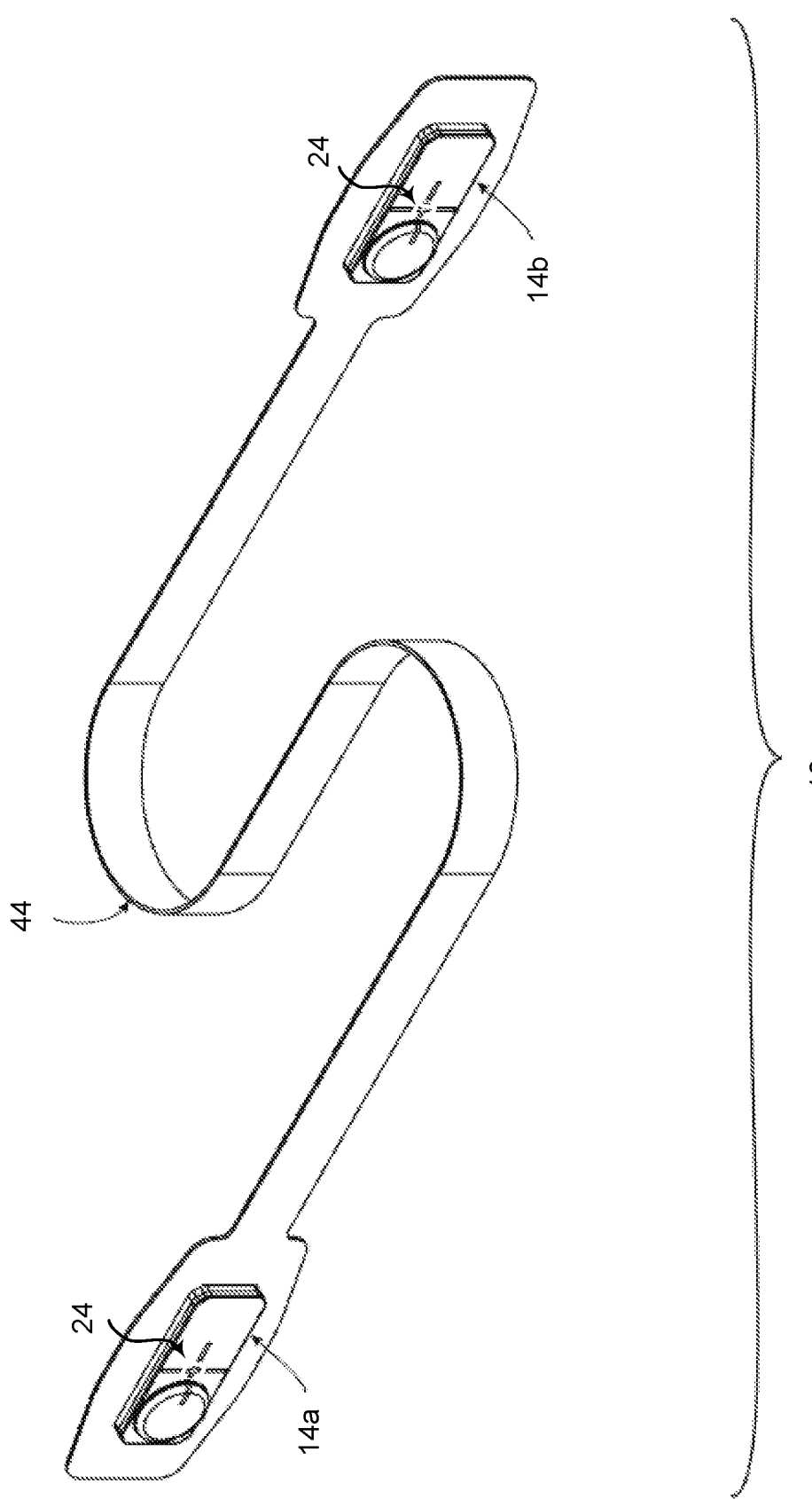
FIG. 6 is an embodiment of an electromagnetic fiducial element assembly having a plurality of electromagnetic fiducial element structures.

FIG. 6 is another electromagnetic fiducial element assembly embodiment 10a having a plurality of electromagnetic fiducial element 14a, 14b structures. The embodiment of FIG. 6 may be arranged as a belt of any desirable length to wrap around a patient in the vicinity of the patient's torso, for example. The electromagnetic fiducial element assembly embodiment 10a includes a flexible substrate 44. Two electromagnetic fiducial elements 14a, 14b are depicted in the embodiment at opposing ends of the flexible substrate 44. One, three, or some other number of electromagnetic fiducial elements 14 could also be included. The electromagnetic fiducial elements 14 could be located at any desirable position of the flexible substrate 44.

In some cases, the flexible substrate 44 includes wires, traces, conductors, sensors, power sources, or other structures. The conductive elements may be used as a means to provide electrical, communicative, or other signal coupling between electromagnetic fiducial elements 14 and in addition, or in the alternative, between electromagnetic fiducial elements 14 and some other computing device. If the flexible substrate 44 includes optional exemplary sensors, the sensors may be used to provide heart signals, temperature signals, capacitive signals, galvanic response signals, "belt attached to the patient" or "belt removed from the patient" signals, step counters, or any other type of sensors.

Figure 7:
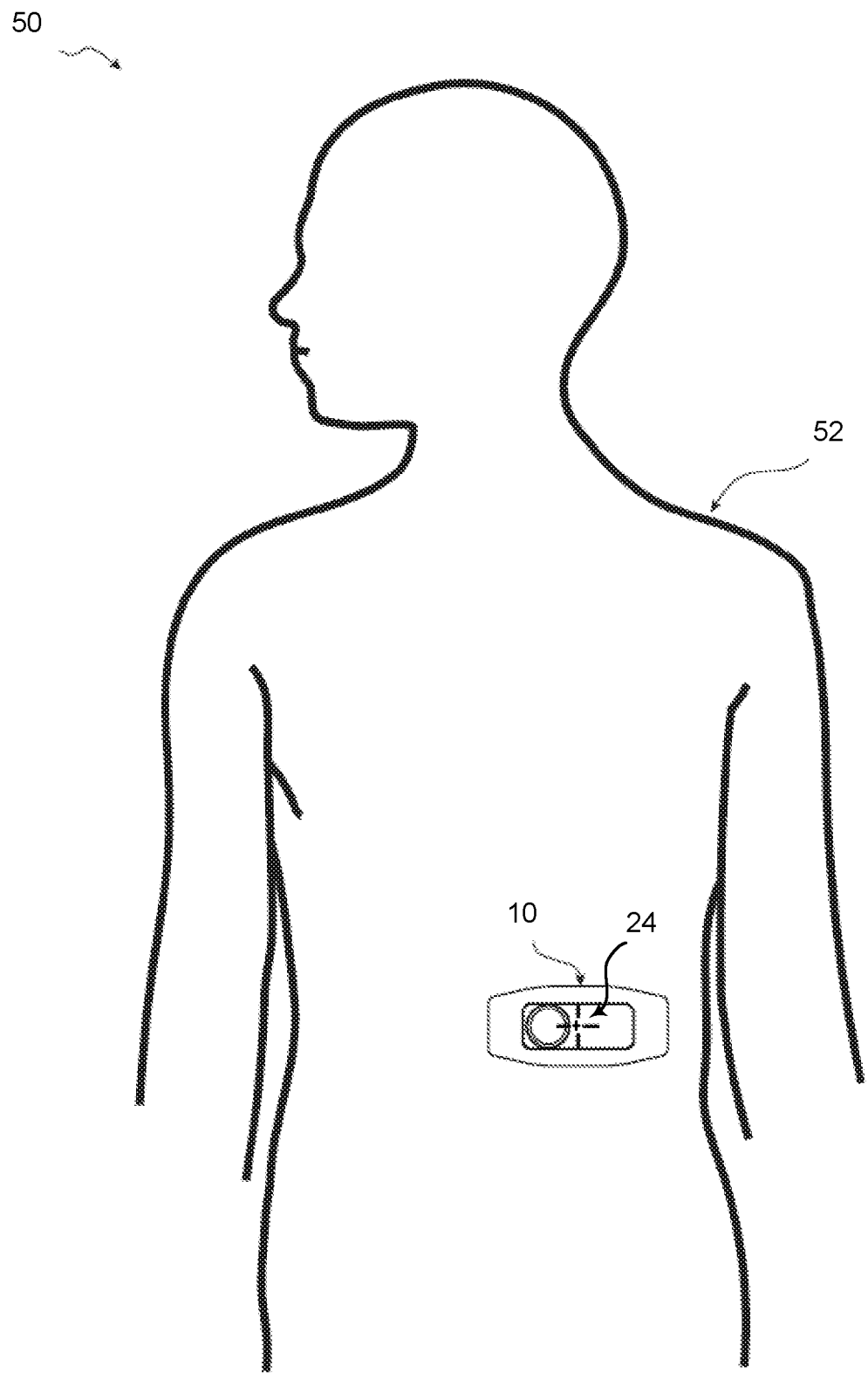
FIG. 7 is a human patient with an electromagnetic fiducial element assembly embodiment removably attached to the patient's body.

FIG. 7 is a human patient 50 with an electromagnetic fiducial element assembly 10 embodiment removably attached to the outer surface of the patient's body 52. In medical procedures described herein, the electromagnetic fiducial element assembly 10 will be suitably affixed to the skin of the patient 50. The electromagnetic fiducial element assembly 10 may remain in place for a few minutes, hours, several days, or for some other period of time as desired for the medical procedure. In FIG. 7, the electromagnetic fiducial element assembly 10 is affixed in a region of patient's lower torso, however, this one or another electromagnetic fiducial element assembly 10 can be mounted in any other area. For example, if the patient 50 has an artificial limb or some other prosthesis, the electromagnetic fiducial element assembly 10 could also be mounted to the prosthesis. Preferably, the electromagnetic fiducial element assembly 10 will remain in a same position on or about the patient's body during a first medical procedure to capture one or more medical images, and the electromagnetic fiducial element assembly 10 will remain in the exact same, or about the same, position during one or more later medical procedures to track the position of a medical device inside the body of the patient 50 relative to the electromagnetic fiducial element assembly 10.

Figure 8:
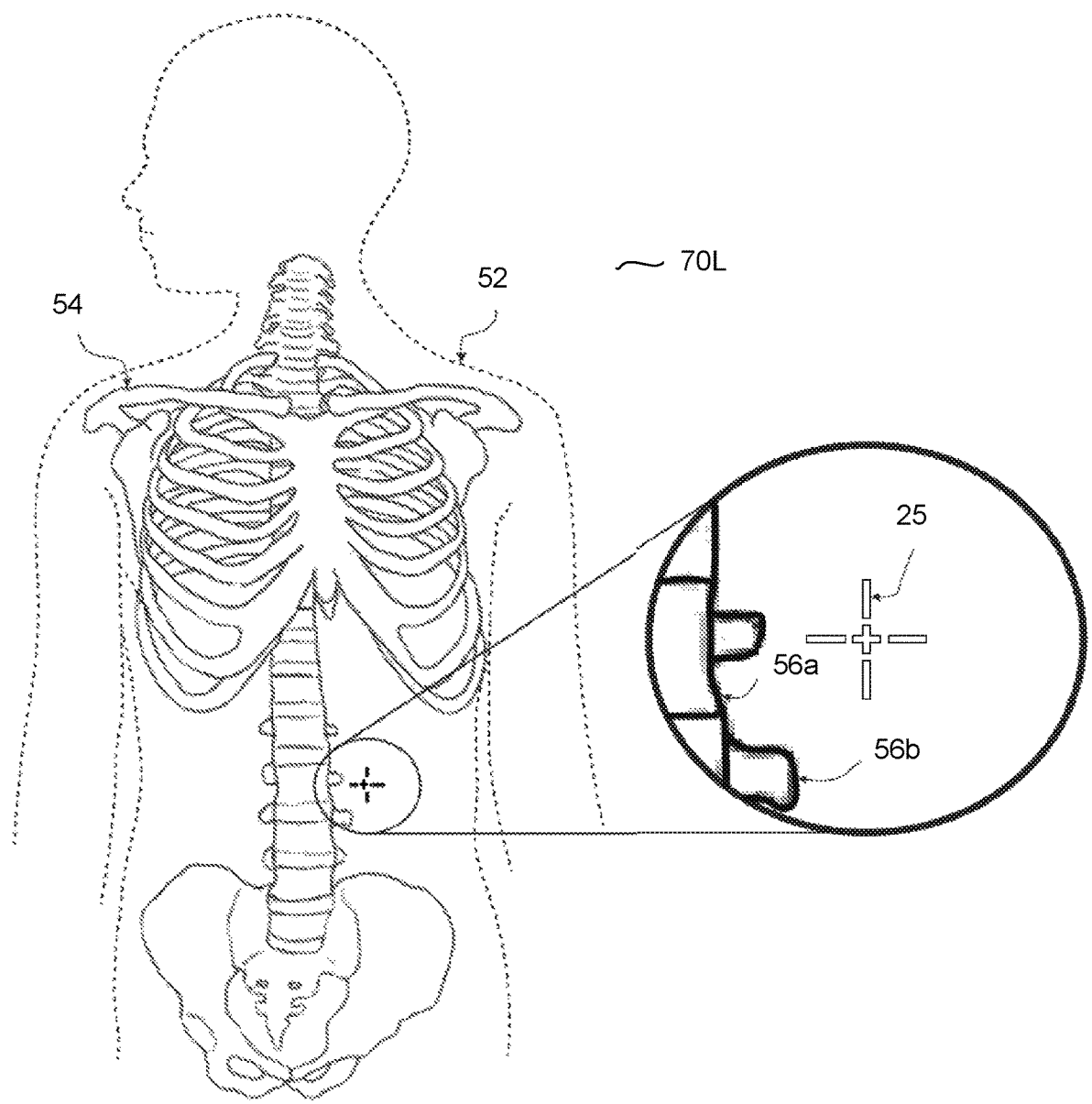
FIG. 8 is a live medical image having a representation of the medically imagable target visibly apparent.

FIG. 8 is a live medical image 70L. A representation 25 of the medically imagable target 24 is visibly apparent in the live medical image 70L. Namely, the target 24 will show as image 25 in the live medical image 70L. The medical image 70L may be captured by a first type of imaging that will image the body of the patient, for example, the bones, layers, or internal organs. This can be carried out using an x-ray procedure, a fluoroscopy procedure, or by some other medical imagining technique (e.g., ultrasound, computed tomography (CT), magnetic resonance imaging (MRI), or the like. Excessive imaging of the patient's body with some types of imaging is harmful to the patient. For example, if the patient is exposed for long periods of time to high powered x-rays, CT scans, or other procedures that impose high levels of electromagnetic radiation, these procedures may cause damage to some biological tissue in the patient. Similarly, excess exposure to ultrasound, particularly high powered ultrasound that is designed to penetrate to deep structures in the body, can also cause damage to the tissue of the patient. Accordingly, in FIG. 8, a live set of images 70L is obtained using a first type of medical imaging of the body tissue itself, after which the set of images is stored.

The outer surface of the patient's body 52 is identified in FIG. 7, and a portion of the skeletal structure 54 of the patient 50 is also identified. In a detail view, about the representation 25 of the medically imagable target 24, two exemplary skeletal structures are identified, which include a first portion of a vertebral body 56a (e.g., pedicle), and a second portion of a vertebral body 56b (e.g., transverse process).

After the live medical image 70L has been obtained, it is stored as a completed, static image 70. See FIGS. 10A and 10B, for example.

In the teaching of the present disclosure, a previously obtained and stored medical image, or a plurality of images, will be used to help a medical practitioner guide a medical instrument to a location inside of a patient's body. Stated differently, the medical practitioner will be provided a stored image or set of images of the body. The body will not be subject to the imaging while the medical practitioner is viewing the stored image. Accordingly, the medical practitioner can observe the image for long periods of time and there is no potential for damage to the tissue of the body since no further imaging is being carried out. Instead, a stored, static image 70 of the body will be provided, and the medical practitioner will visually observe a representation of the medical instrument being displayed as the instrument is tracked on a previously captured medical image 70. The representation 25 of the medically imagable target 24 will be visually apparent in the image at a position relative to the natural structures in the patient's body, which will help the practitioner guide and position the medical device. The electromagnetic fiducial element 14 of the electromagnetic fiducial element assembly 10 (e.g., a first trackable electromagnetic structure) and a different electromagnetic element associated with the medical device being inserted into the patient (e.g., a second trackable electromagnetic structure) will be concurrently tracked. By concurrently tracking both electromagnetic elements in real time, the externally located electromagnetic fiducial element 14 can be used as a reference point to display (i.e., paint, track, overlay, or integrate in some other way) a tracked image of the medical device on the one or more previously captured medical images.

Figure 9:
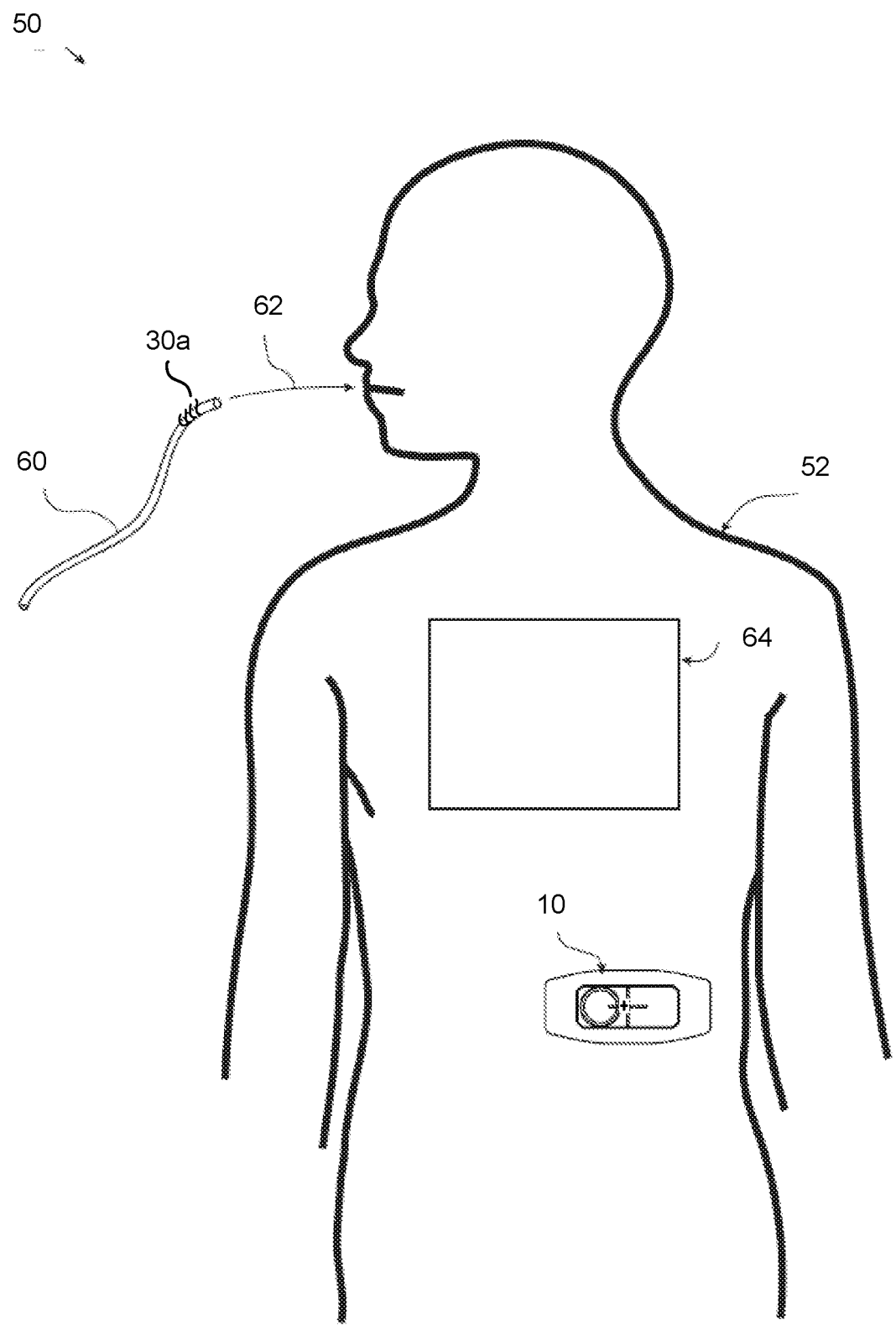
FIG. 9 is the patient of FIG. 7 during a medical procedure in which a medical tube will be guided to a location in the patient's body.

FIG. 9 is the patient 50 of FIG. 7 before proceeding with a medical procedure in which a medical device 60 will be guided to a location in the body of the patient 50. The medical device 60 has an electromagnetic coil assembly 30a associated therewith. The electromagnetic coil assembly 30a has generally the same structure as electromagnetic coil assembly 30, so the details are not provided here. In the embodiment of FIG. 9, the electromagnetic coil assembly 30a is integrated at or near a distal tip of the medical device 60. In other embodiments, one or more electromagnetic coil assemblies may be located in other areas on or near the medical device 60.

In the embodiment of FIG. 9, the medical device 60 is a medical tube that may be used to deliver therapy, capture a sample, or for some other purpose. In other cases, the medical device may be a needle, a wire, a stylet, a catheter such as a Peripherally Inserted Central Catheter (PICC), a tracheal tube, an implantable device, a cannula, or some other structure for temporary or permanent placement. In some cases, the medical device 60 is a hollow tube-like device. In some cases, the medical device 60 is an elongated solid member. In some cases, the medical device 60 takes another form. Many other medical device embodiments are of course contemplated.

The medical device 60 has an associated electromagnetic coil assembly 30a, which may be on the distal tip of the medical device 60, some other portion of the medical device 60, or in proximity to the medical device 60 even if not attached to the medical device 60.

Starting path 62 in FIG. 9 shows that the medical device 60 will be advanced into the mouth of the human patient 50. In other embodiments, the medical device 60 is advanced into the patient's body through a different natural or created orifice. For example, the medical device may enter the body through the nose, an incision, a puncture, or some other natural or non-natural opening.

A sensor 64 is positioned by the medical practitioner in proximity to the patient 50. In FIG. 9, the sensor 64 is movably positioned on the patient's chest. The sensor 64 is a device for tracking one or more electromagnetic tracking elements. This sensor 64 does not image the patient's body. Rather, the sensor 64 tracks and creates an image of the trackable electromagnetic element 30a. The body 52 of the patient is subject to the sensor 64, which can be a passive type of sensing that is tuned to the trackable electromagnetic element 30a, and which does not a produce potentially damaging output to the body 52. In other embodiments, the sensor 64 is not passive, but it is a very low power sensor. Accordingly, the body of the patient can be exposed to the sensor 64 for long periods of time without suffering potential significant harm to the tissues. The sensor is further described with respect to FIG. 14.

Figure 10A:
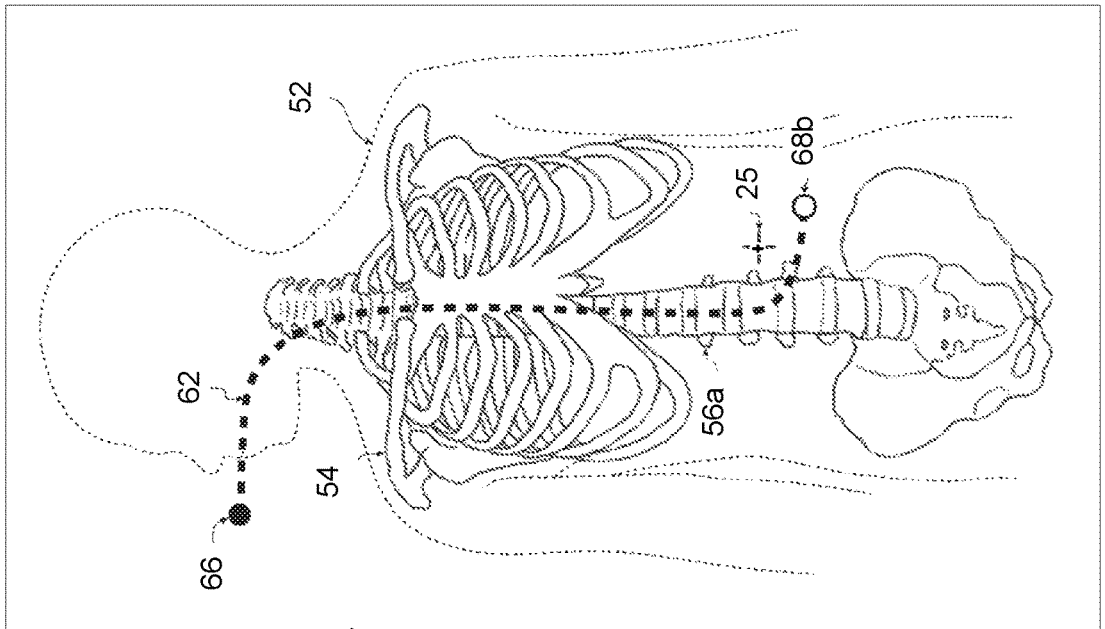
FIGS. 10A and 10B are displays of a stored medical image previously captured during the procedure of FIG. 8 and having displayed thereon the tracking of a medical device in the body of the patient.
Figure 10B:
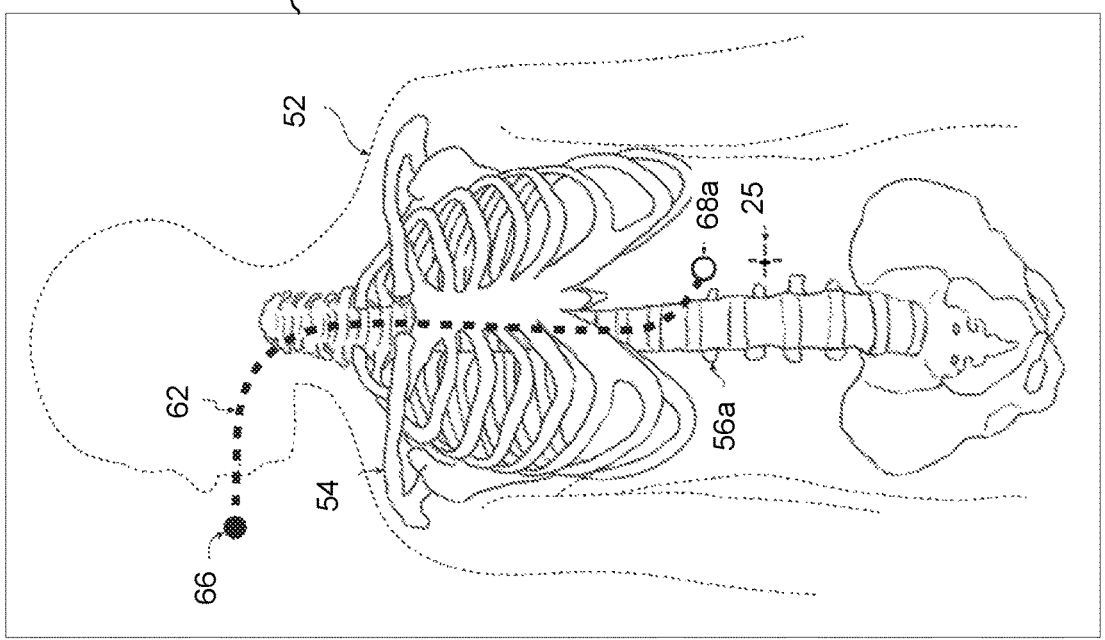
Figure 15:
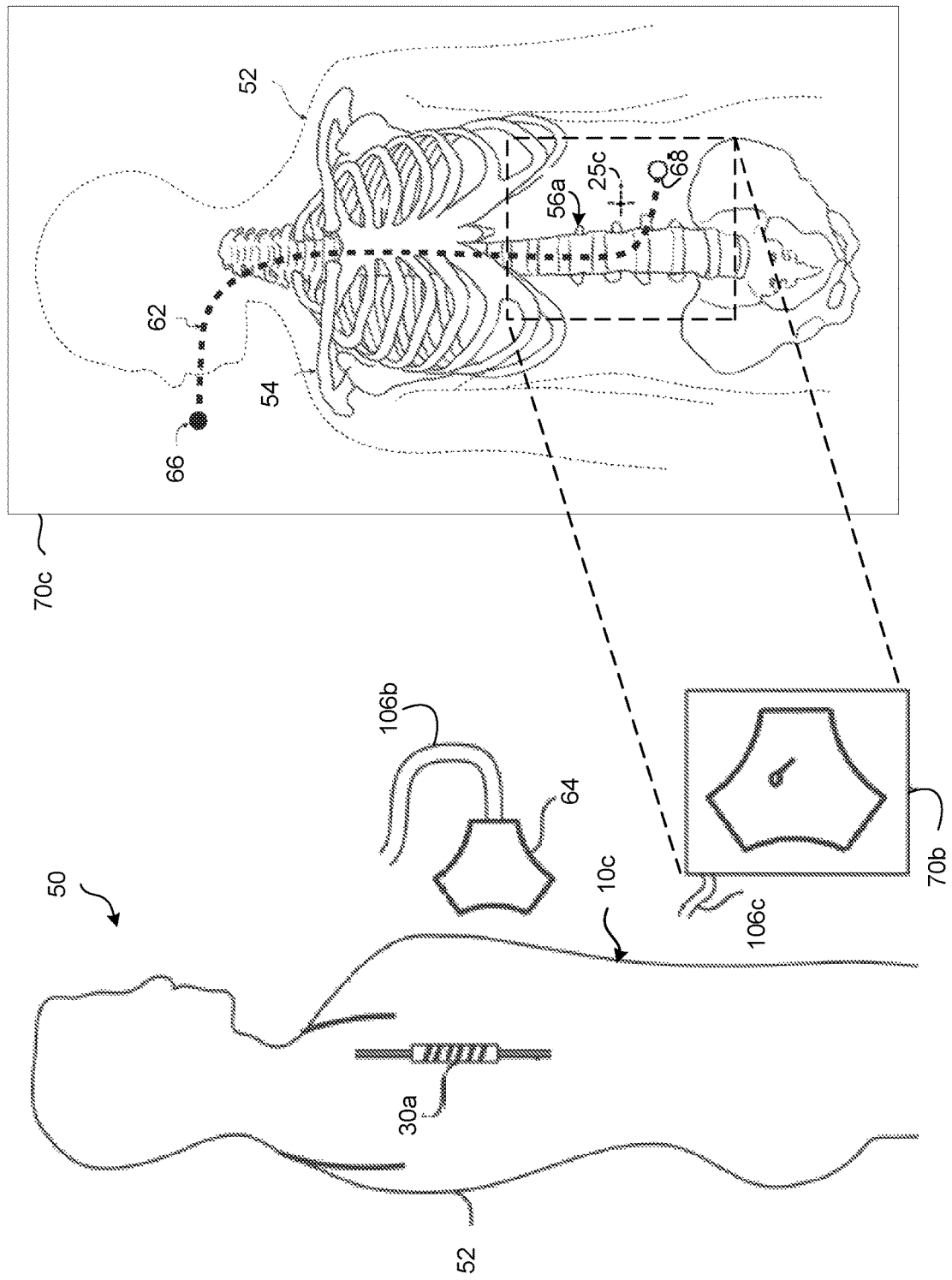
FIG. 15 illustrates a medical procedure using a trackable electromagnetic element in a medical environment including a system for detecting the position of a medical instrument within the body of a patient and displaying a representation of the medical instrument on a previously stored, static image of the patient, according to one embodiment.

FIGS. 10A and 10B are a stored, currently static medical image 70 having displayed thereon the track of a medical device 60 into the body of the patient 50 (FIG. 9). This can be the stored version of the live image 70L obtained as described in FIG. 8. In the medical image 70, the outer surface of the patient's body 52 is identified, and a portion of the skeletal structure 54 is identified. Also identified in the medical image 70 of both FIG. 10A and FIG. 10B are a first portion of a vertebral body 56a (e.g., pedicle) and the representation 25 of the medically imagable target 24. The body 52 of the patient is in a different location than the stored image 70, preferably in a place in which the medical practitioner can move the medical device 60 (FIG. 9), which has the trackable electromagnetic element 30a, while at the same time, observe the stored image 70. The sensor 64, working also to track one or more reference electromagnetic coil assemblies 30, permits the trackable electromagnetic element 30a to be correctly represented relative to the static image 70 as the path of the medical device 60 is displayed as an overlay on the static image 70. FIG. 15 provides a additional examples and explanations. FIG. 10A depicts the start of the medical procedure of guiding the medical tube 60 of FIG. 9 into the patient's body using two electromagnetic coil assemblies (e.g., a reference electromagnetic coil assembly 30 of the electromagnetic fiducial element assembly 10 and an electromagnetic coil assembly 30a of the medical device 60) and the previously acquired medical imagery of FIG. 8 having the representation 25 of the visibly apparent medically imagable target 24. In FIG. 10A, the medical device has been advanced from a starting location 66 to a first ending location 68a.

FIG. 10B is the medical procedure having guided the medical tube of FIG. 9 into the patient's body from the starting location 66 to a different, second ending location 68b. By tracking two electromagnetic coil assemblies (e.g., reference electromagnetic coil assembly 30 of the electromagnetic fiducial element assembly 10 and electromagnetic coil assembly 30a of the medical device 60), the sensor 64 is able to determine its own position relative to the two-dimensional medical image 70, generate additional position information in two dimensions, and paint or otherwise display the track of the medical device 60 onto the medical image 70 using the additional position information. In this way, for example, the actual motion of the medical device 60 is drawn, painted, or otherwise integrated as a representation in real time on the two-dimensional medical image or video.

Figure 11:
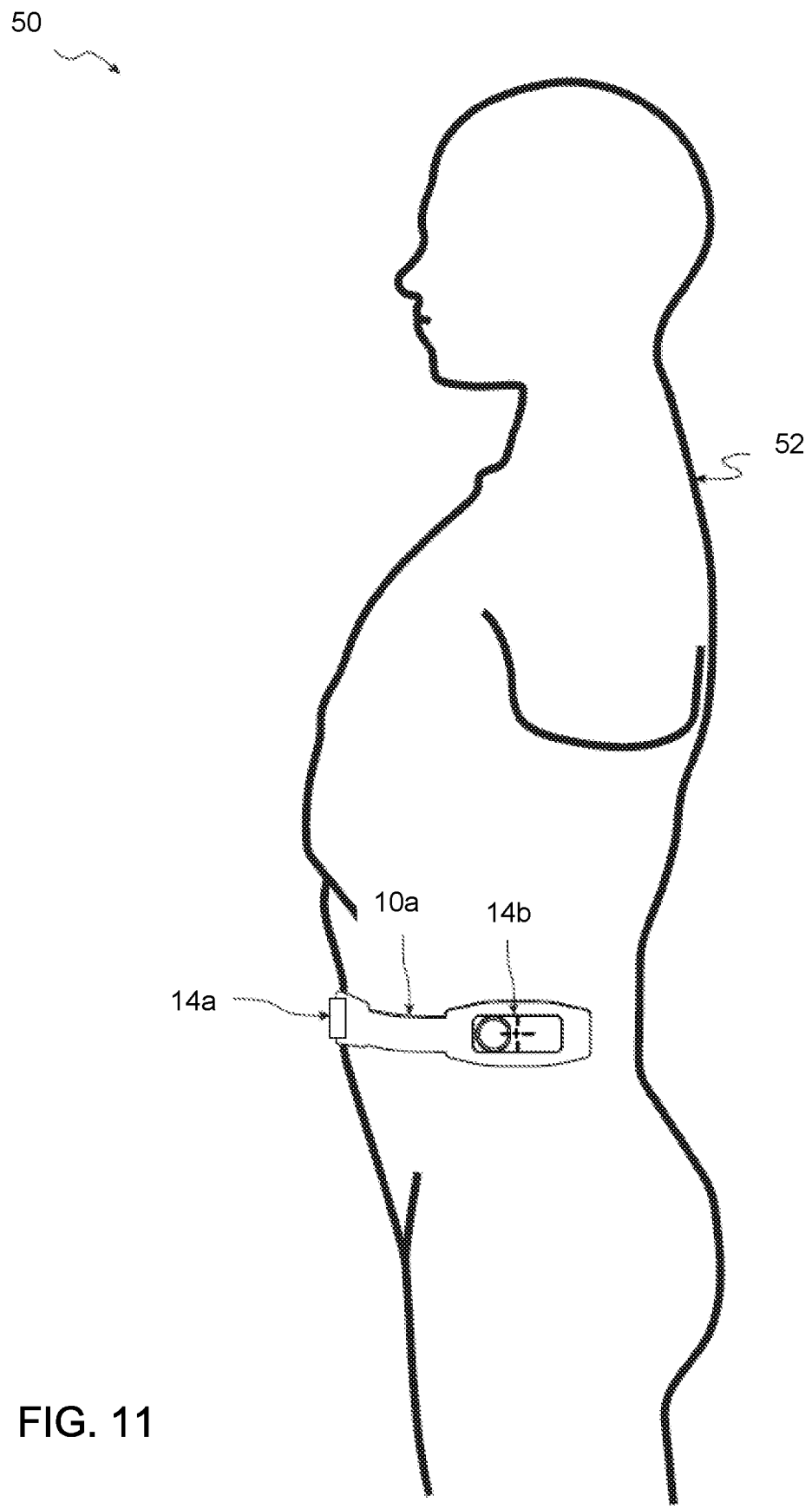
FIG. 11 is a human patient in preparation for a medical procedure using the electromagnetic fiducial element assembly embodiments as described herein.

FIG. 11 is a human patient 50 in preparation for a medical procedure using the electromagnetic fiducial element assembly embodiment of FIG. 6. In the embodiment of FIG. 11, the electromagnetic fiducial element assembly 10a has two electromagnetic fiducial elements 14a, 14b. In some embodiments, one, three, or some other number of electromagnetic fiducial elements 14 are included. By tracking multiple electromagnetic coil assemblies (e.g., two separate and distinct reference electromagnetic coil assemblies 30 of the electromagnetic fiducial element assembly 10a that are positioned outside of the patient's body, and an electromagnetic coil assembly 30a of the medical device 60), the sensor 64 is able to generate position information and thereby present one or more images representing the track of the medical device 60 relative to the reference electromagnetic fiducial elements 14a, 14b that are visibly apparent in the medical image. In this way, for example, the actual motion of the medical device is drawn, painted, or otherwise represented in real time in three dimensions in a series of medical images.

Figure 12A:
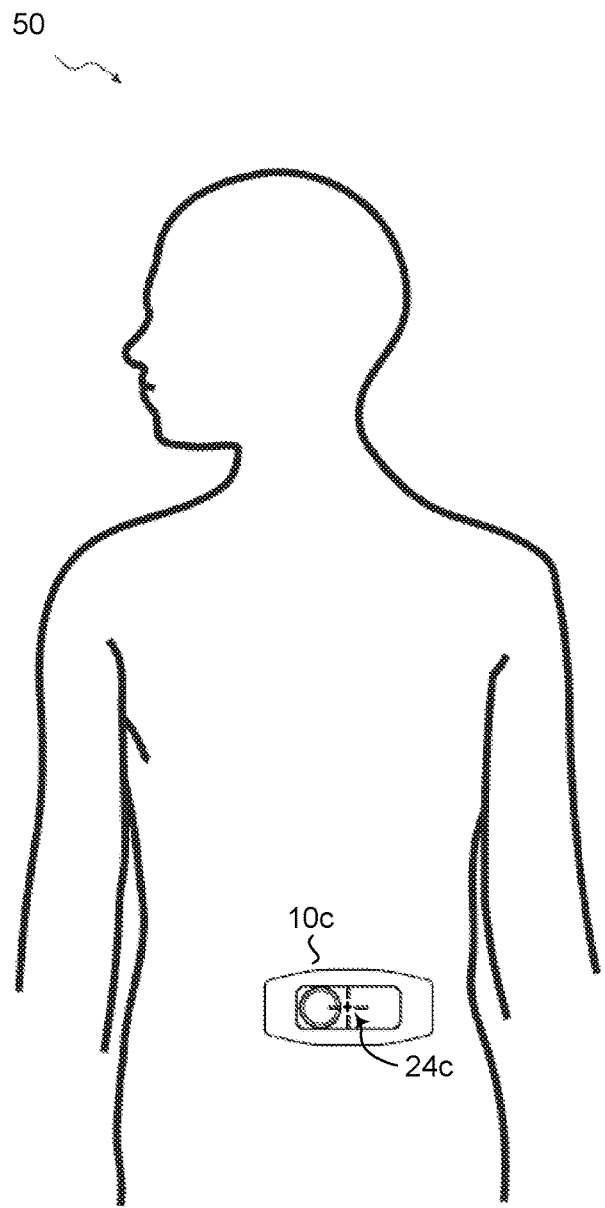
FIGS. 12A-12B are a human patient having one or more electromagnetic fiducial element assembly embodiments removably affixed to the patient's body in preparation for a medical procedure as described herein.
Figure 12B:
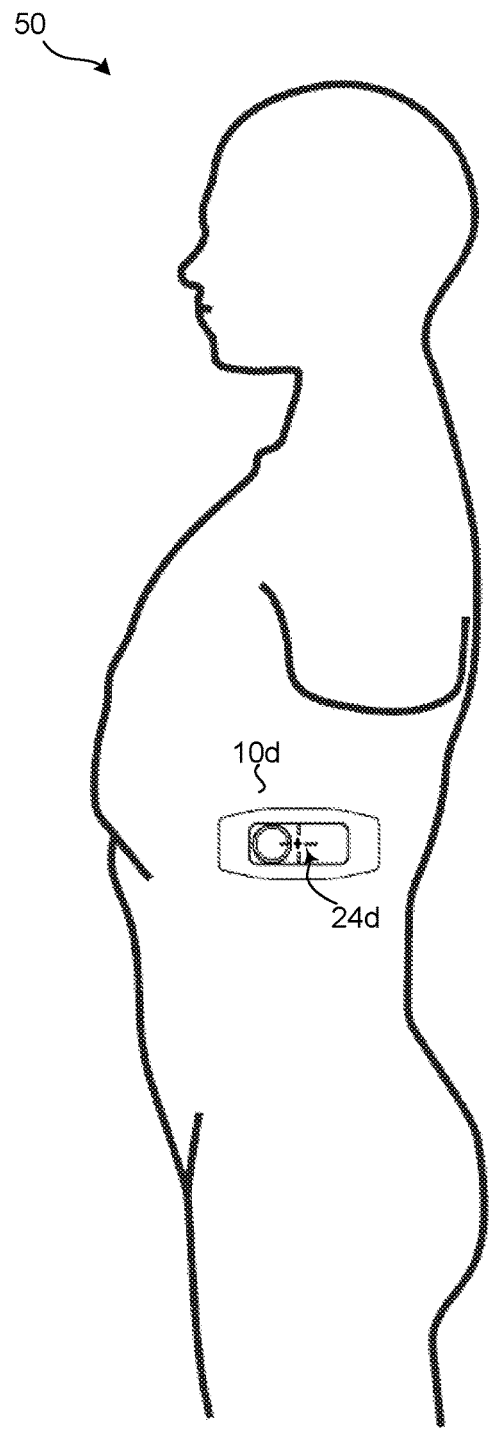

In at least some embodiments of FIG. 11, three or more electromagnetic coil assemblies are employed in a medical procedure. For example, two coil assemblies 30 (FIG. 4) are configured in the electromagnetic fiducial element assembly 10a and a third coil assembly 30a (FIG. 9) is configured in a medical device 60. By tracking three different coil assemblies, relative to each other, an acceptably exact location of each coil assembly relative to the other coil assemblies can be more accurately determined, and the relative location of the medical instrument inside the patient's body can also be determined with acceptable accuracy. Different tracking techniques, including triangulation algorithms, trilateration algorithms, multilateration algorithms, probabilistic matching algorithms, and the like, can be used to identify the location of one or more electromagnetic coil assemblies relative to each other, relative to body structures, and alternatively or additionally in a selected coordinate space, with acceptable accuracy. More techniques are described International Application No. PCT/US2017/014395 to Andreason et al. that is incorporated herein by reference FIGS. 12A-12B are the human patient 50 having one or more electromagnetic fiducial element assembly 10 embodiments removably affixed to the patient's body. The representations illustrate that an electromagnetic fiducial element assembly 10 can be located in any desirable location on the patient's body. The representations further illustrate that two or more electromagnetic fiducial element assemblies 10 can be located in any desirable locations on the patient's body. In FIG. 12A, a first electromagnetic fiducial element assembly 10c embodiment is located on the front lower torso of the patient 50. The medically imagable target 24c is identified. In FIG. 12B, a second electromagnetic fiducial element assembly 10D embodiment is located on the side torso of the patient 50. The medically imagable target 24d is identified. Using the medically imagable target, the sensor 64 (FIG. 9) that tracks the electromagnetic assemblies can register the coordinate system of the sensor 64 to the coordinate system of the two-dimensional or three-dimensional (2D or 3D) medical image data. That is, when a single electromagnetic fiducial element assembly 10 is used in combination with an electromagnetic coil assembly 30a on the medical device 60, the sensor 64 can be registered to a 2D image, and the position of the medical device 60 can be tracked in real time on the 2D image. And in addition, or in the alternative, when two or more electromagnetic fiducial element assemblies 10 are used in combination with an electromagnetic coil assembly 30a on the medical device 60, the sensor 64 can be registered to the 3D image data, and the position of the medical device 60 can be tracked in real time in 3D space on the series of images.

Figure 13:
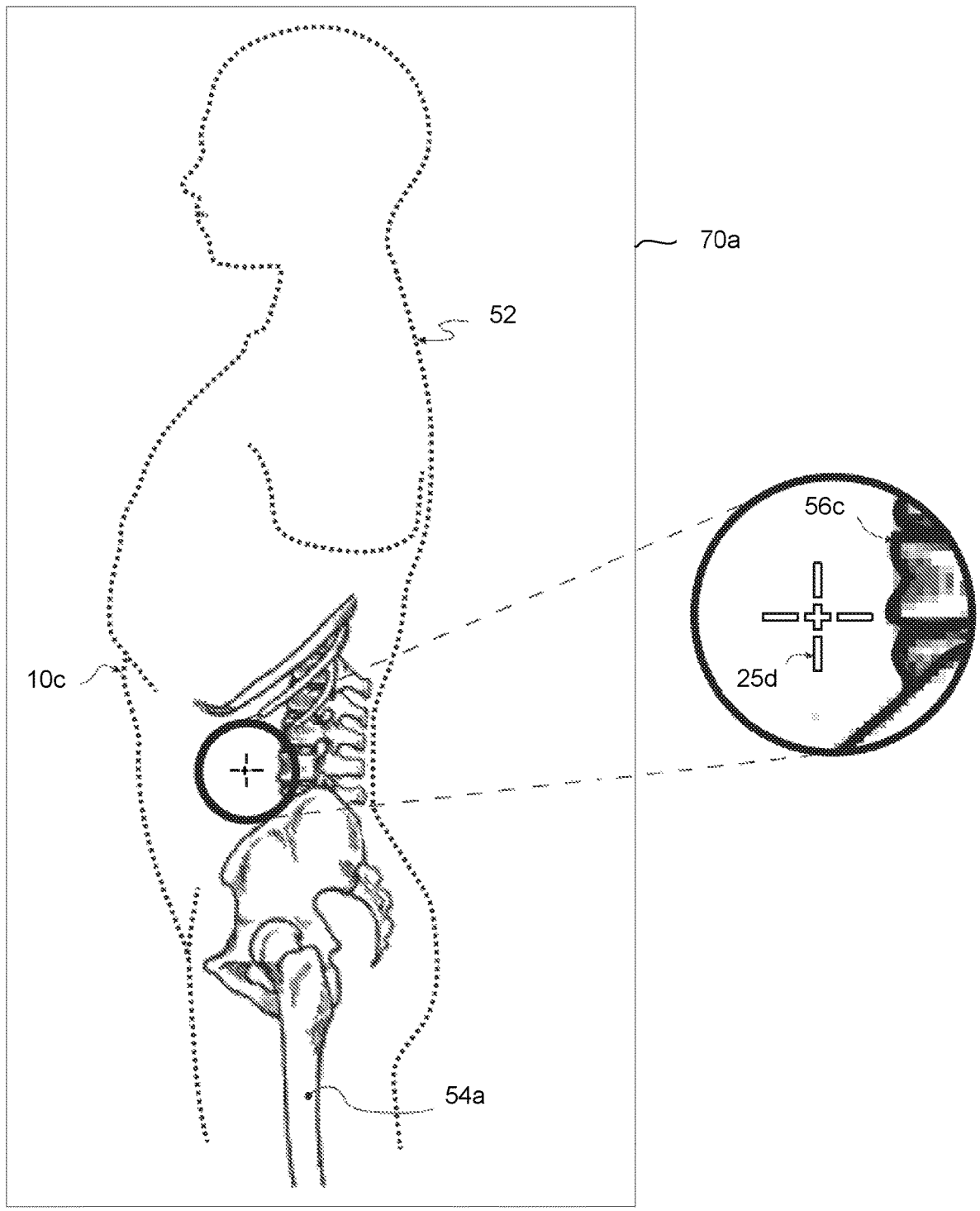
FIG. 13 is a display of a stored medical image having the medically imagable target visibly apparent.

FIG. 13 is another medical image 70a having the medically imagable target 24d (FIG. 12B) visibly apparent as a representation 25d. The representation 25d depicted in FIG. 13 is caused by an attenuation of energy (e.g., x-rays) from the medically imagable target 24d on the electromagnetic fiducial element assembly 10D of FIG. 12B. In a detail view portion of FIG. 13, the representation 25d is visible in proximity to a vertebral body 56c, which is also apparent in the medical image 70a.

Figure 14:
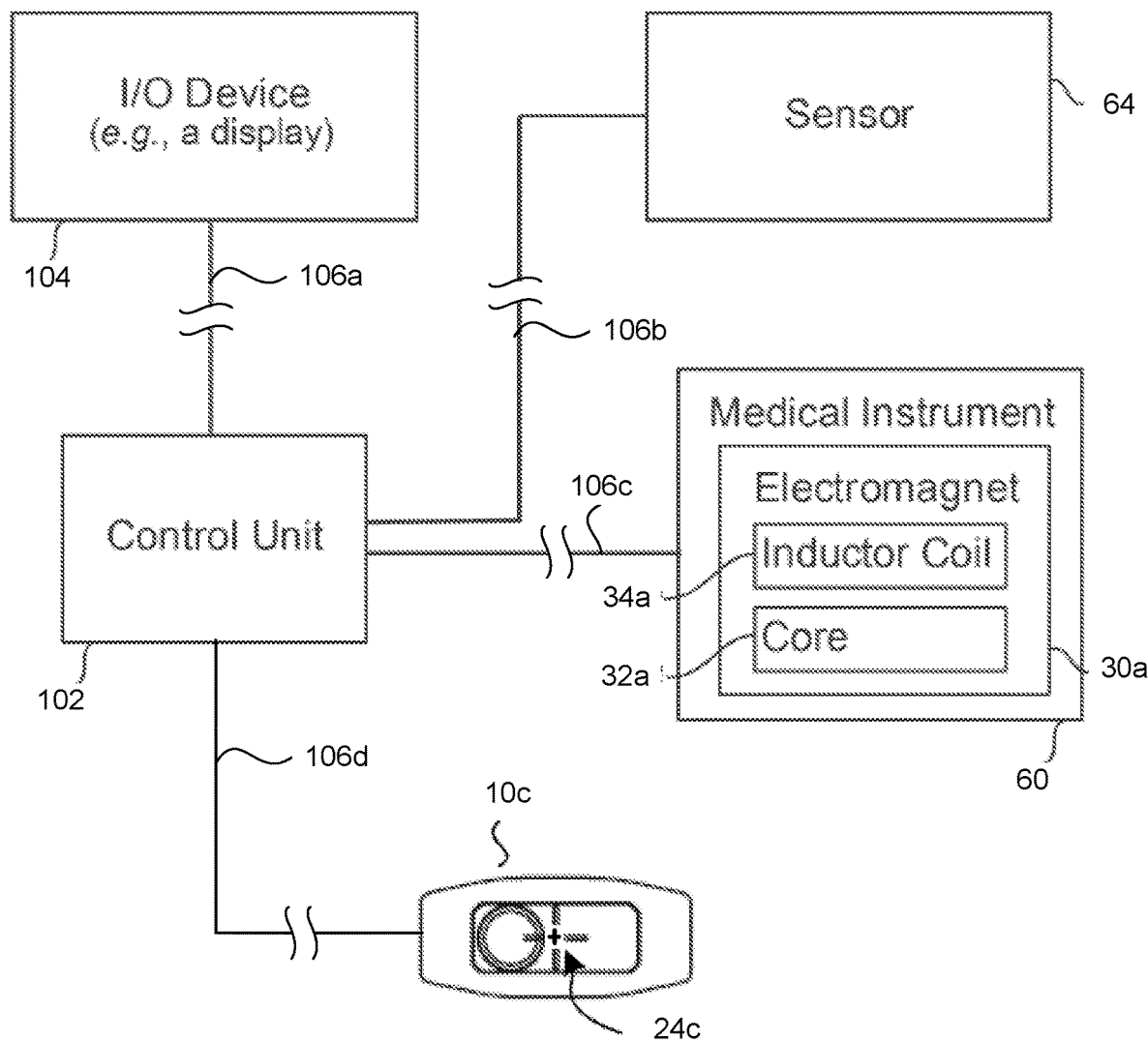
FIG. 14 is a block diagram of a system for detecting the position of trackable electromagnetic elements according to one embodiment.

FIG. 14 is a block diagram of a system 100 for detecting the position of trackable electromagnetic elements according to one embodiment. The system 100 includes an embodiment of a medical device 60. The medical device 60 has an integrated or otherwise associated electromagnetic coil assembly 30a. The electromagnetic coil assembly 30a has a core 32a and a coil magnetic section 34a, which may otherwise be referred to as an inductor coil, a coil, or another like term.

In some cases, one or more components of the system 100 are integrated. In other cases, two or more components of the system 100 are separate and distinct. For example, in at least one embodiment, the sensor 64, the control circuit 102, and the user interface 104 are arranged in a single package (e.g., a single housing). In other embodiments, individual circuits of the components are separate and distinct while also cooperatively coupled. For example, in at least one embodiment, the control circuit 102 includes one or more circuits integrated with the user interface 104 and one or more circuits integrated with the sensor 64.

Also depicted in FIG. 14 is an electromagnetic fiducial element assembly 10c. The electromagnetic fiducial element assembly 10c is along the lines of the electromagnetic fiducial element assembly 10 in FIGS. 1-4 and other figures in the present disclosure. The electromagnetic fiducial element assembly 10c includes a medically imagable target 24c marking, a coil drive printed circuit board (not shown), and an electromagnetic coil assembly (not shown).

Sensor 64 includes one or more magnetic sensors arranged to detect one or more magnetic fields generated by one or more electromagnetic coil assemblies 30, 30a. The sensor 64 is arranged to detect certain parameters of the generated magnetic field such as field strength and polarity (i.e., direction). The sensor 64 generates one or more sensor signals indicative of the parameters of each magnetic field generated by a respective electromagnetic coil assembly 30, 30a. The position of the medical device 60, and in some cases the position of two or more medical devices 60, along with orientation, motion, and other location-based information can be determined based on the parameters of a magnetic field generated by each electromagnet structure.

Operations of the sensor 64 are in some cases coordinated by one or more control circuits 102 such that parameters to direct certain sensor functions are applied in cooperation with parameters to direct excitation of the electromagnetic coil assemblies 30, 30*a*. In at least one embodiment, the control circuit 102 directly drives, or causes to be driven, a coil of the respective electromagnetic coil assemblies 30 and 30*a* with an excitation signal having a frequency between about 50 Hz and about 10,000 Hz. In at least one of these embodiments, the coil is driven with an excitation signal having a frequency less than 500 Hz, such as between about 200 Hz and 500 Hz. The excitation signal may have, for example, a frequency of about 330 Hz. Different frequencies and ranges of frequencies are also contemplated.

In some cases, the lower end of the acceptable frequency range for an exemplary electromagnetic element is determined by electronics noise, update rate, and other factors. In some cases, the upper end of the acceptable frequency range for an exemplary electromagnetic apparatus is based at least in part on the physical dimensions (e.g., diameter) of the core 32 and the characteristics of the coil wire in the coil electromagnet section 34. For example, a smaller core may permit a higher frequency and larger coil wire may permit more current. At least one other set of factors that may contribute to an acceptable frequency range is a size, shape, and placement of a ground plane in the sensor 64.

In some embodiments, a plurality of electromagnetic coil assembly embodiments located in the same general vicinity of each other may be cooperatively operated using excitation signals having different frequencies, phases, signatures, or other different characteristics. In this way, each different electromagnetic element will generate a different magnetic profile (e.g., signature) when detected and tracked by a sensor 64 (e.g., magnetic field sensing device). In some embodiments, the number of concurrently trackable electromagnetic elements is limited by the processing speed of the sensor 64, the refresh rate of the sensor 64, the selected excitation frequencies, or other such parameters.

The control circuits 102 may be formed, in whole or in part, in the sensor 64, in an electromagnetic fiducial element assembly 10, in a medical device 60, or in some other device or devices.

Control circuit 102 may include multiple discrete control circuit portions. Control circuit 102 can include one or more microcontrollers, one or more microprocessors, one or more memory devices, one or more voltage sources, one or more current sources, one or more analog-to-digital converters, one or more digital-to-analog converters, and/or one or more wireless transceivers. One or more of these components can collectively make up the control circuit 102.

Control circuits 102 are described as driving an inductor coil 34 of an electromagnetic coil assembly 30, 30*a* with an excitation signal or applying an excitation signal to an inductor coil 34*a*. The control circuit 102 can accomplish this by directly applying the excitation signal to the inductor coil 34*a*. Alternatively, the control circuit 102 can accomplish the excitation of the coil 34*a* by indirectly by controlling a voltage source that applies a voltage signal to the inductor coil 34*a* or by controlling a current source that supplies a current signal to the inductor coil 34*a*. Those of skill in the art will recognize, in light of the present disclosure, that the control circuit 102 can generate, pass, or otherwise apply an excitation signal to the inductor coil 34 of an electromagnetic coil assembly 30, 30*a* in many other ways. All such other ways are within the scope of the present disclosure.

In some embodiments, for example, the control circuit 102 both controls the electric current that will be driven through an inductor coil, and the control circuit 102 calculates location-based information (e.g., position, orientation, motion, timing, and the like) of a particular medical device 60. The control circuit 102 receives and analyzes one or more sensor signals from the sensor 64 and generates the location-based information, such as the position of the medical device 60, based on the one or more sensor signals. In this way, sensor 64 can identify and track the position of medical devices 60 in two or three dimensions and the orientation of medical devices 60 relative to a reference point such as one or more electromagnetic fiducial element assemblies 10.

User interface 104, in at least one embodiment, includes a display that is wired or wirelessly coupled to the sensor 64. The user interface 104 presents a visual representation of the position of one or more medical devices 60 within the body of the patient 50 by overlaying a representation of the medical device 60, or some component of the medical device 60, onto a previously captured medical image 70. In this way, with acceptable accuracy, the visual representation of the position of the medical device 60, which is painted on the medical image 70, enables a medical practitioner to know the position of the medical instrument 60 in real time within the body of the patient 50. This in turn can enable the medical practitioner to correctly perform medical procedures on the patient 50. Ones of ordinary skill in the art will recognize that such teaching may also be applied to a series of medical images (e.g., a video, an MRI, a CT scan, or any other such series of images)

In some embodiments, the control circuit 102 generates a video signal (e.g., a stream of medical images) and outputs the video signal to the user interface 104 (e.g., a display). The video signal includes a representation of the position of one or more medical instruments 60 within the body of the patient overlaid or otherwise integrated in the previously captured stream of medical images 70. The video signal can also include position data that can be displayed or otherwise presented via the user interface 104. The position data can include text that indicates numerical coordinates representing the position, orientation, and motion of the medical device 60. The video signal displayed or otherwise presented via the user interface 104 can present in real time both a visual representation of the position of the medical instrument 60 within the body of the patient 50 and certain position data that indicates the position of the medical instrument 60 within the body of the patient 50.

The broken lines 106*a*, 106*b*, 106*c*, 106*d* between the control unit 102 and the user interface 104, sensor 64, medical device 60, and electromagnetic fiducial element assembly 10*c* may individually or collectively be referred to as conduit 106. Conduit 106 indicates that communications or other signaling between the devices may be over a wired medium, a wireless medium, a combination medium, or any other communicative means. In this way, these broken lines 106*a*-106*d* depict an electrical, communicative, or electro-communicative conduit 106 that is used to pass power signals, control signals, data signals, or some other type of electromagnetic signals between devices of the system 100. In the embodiment of FIG. 14, conduit 106 is arranged to pass or otherwise direct electrical signaling information to the low-frequency electromagnet structures (e.g., electromagnetic fiducial element 14 of electromagnetic fiducial element assembly 10c and electromagnetic coil assembly 30a of medical device 60). Conduit 106 may pass electrical signals in any one or more of a point-to-point arrangement, serial arrangement, parallel arrangement, networked arrangement, and alternatively, in some other arrangement.

Conduit 106 may be used to pass signaling information between the magnetic field sensing device (e.g., sensor 64) and user interface 104 (e.g., a display). Conduit 106 may in addition, or in the alternative, pass signaling information between the magnetic field sensing device and one or more of the low-frequency electromagnet structures. The signaling information may include power signals, control signals, data signals, or other signals.

In some embodiments, any one or more of the electromagnetic fiducial element assembly 10c, medical device 60, magnetic field sensing device (e.g., sensor 64), control circuit 102, and user interface 104 may include one or more wireless transceivers arranged to communicate data between the devices. In these and other embodiments, the devices may include one or more wireless transceivers arranged to wirelessly communicate information (e.g., information to generate a particular excitation signal) to drive the low-frequency electromagnet elements. In some cases, the control circuit 102 may be arranged to provide any one or more of programming instructions, data, excitation signals, and other such information to the controller 40 (FIG. 4) in the electromagnetic fiducial element assembly 10c.

FIG. 15 illustrates an example of using a trackable electromagnetic element 10c in a medical environment according to one embodiment. A system 100 of the type described herein is deployed in the environment of FIG. 15 to detect the position of a medical instrument 60 within the body of patient 50. Patient 50, and the outer surface 52 of the patient 50, are identified in FIG. 15.

Prior to beginning the medical procedure, a medical image 70c is captured and stored. The medical image 70c in FIG. 15 is an x-ray image. In other embodiments, however, medical image data may include any number of medical images from any number of medical imaging modalities. The medical image 70c shows an outline of patient 50 and identifies the outer surface 52 of the patient 50. A first internal portion of the patient's skeletal structure 54 and a second internal portion of the skeletal structure (i.e., a vertebral body 56a) are readily apparent. Also readily apparent in the medical image 70c is a representation 25c of the medically imagable target 24c of the electromagnetic fiducial element assembly 10c of FIG. 12A.

As can be seen in FIG. 15, the stored image 70c is provided adjacent to the patient as a static image of the body 52 to be viewed by the medical practitioner. While the medical practitioner is viewing the image 70c, the medical device bearing the trackable electromagnetic element 30a is advanced into the patient's body. The sensor 64 tracks the trackable electromagnetic element 30a using, for example, techniques described in the application incorporated herein by reference. Tracking information is generated by sensor 64 in front of the live body 52 of the patient, and a representation of the medical instrument generated by the sensor 64 is overlaid on a displayed image 70c. The patient 50 is undergoing an active, live procedure with the trackable electromagnetic element 30a while at the same time, the results of the movement of the medical device are displayed on the static image 70c. The patient 50 therefore is not exposed to the high energy that was used to create the image 70c during this earlier imaging procedure. Accordingly, the movement of trackable electromagnetic element 30a can be carried out for an extended period of time in the live body of the patient 50 as an active procedure, while the exact location inside the body can be seen and known by looking at the previously captured, static image 70c. During the medical procedure, which begins after the medical image 70c has been captured, the medical device 60 is advanced into the patient's mouth. A sensor 64 is movably arranged on the outer body 52 of the patient 50. The medical sensor 64 detects and interprets signals from magnetic fields produced by the electromagnetic coil assembly 30a of the medical device 60 and the electromagnetic coil assembly (not shown) of the electromagnetic fiducial element assembly 10c. In real time, as the medical device 60 is advanced into the patient from a starting location 66 to an ending location 68, the control circuit 102 overlays a representative path of the medical device 60 onto the previously captured medical image 70c. In the embodiment of FIG. 15, a control circuit 102 (not shown), is in wired communication 106b with the sensor 64 and in wired communication 106c with the user interface (not shown) that presents the medical image 70c. Different communicative arrangements may be implemented in other embodiments.

A non-limiting method of use embodiment describing a medical procedure is now described. In the embodiment, a plurality of electromagnetic structures are described including one or more electromagnetic fiducial element assemblies 10. For the sake of brevity and clarity in the description of the method, the electromagnetic fiducial element assemblies 10 are arranged and appear as depicted in the figures. Several features, which are optional or which can be optionally arranged, are described with certainty in this embodiment, but these features are not so limited in practice.

A first electromagnetic fiducial element assembly 10 is a single use device that is removably affixed on the patient's body in a desired location. The electromagnetic fiducial element assembly 10 is optionally secured with adhesive in this case, but other affixation means are also considered including sutures, staples, clamps, and the like. Optionally, a second electromagnetic fiducial element assembly 10 is removably affixed to the patient's body in a second desired location. A single electromagnetic fiducial element assembly 10 permits registration of the coordinate system of the sensor 64 to the coordinate system of a two-dimensional (2D) medical image and tracking a medical device on the 2D medical image. Two electromagnetic fiducial element assemblies 10 permits registration of the coordinate system of the sensor 64 to the coordinate system of three-dimensional medical imagery and tracking a medical device in the 3D medical imagery. In cases where two electromagnetic fiducial element assemblies 10 are used, each device may operate independently, or each device may operate cooperatively.

In this exemplary discussion, a fiducial element assembly 10 is between about 1.5 inches and about 5.0 inches long, between about 0.5 and about 3.0 inches wide, and between about 0.25 and about 1.0 inches tall. The fiducial element assembly 10 has a bondable strip 12 plastic substrate carrying a bonding means 26 adhesive along the lines of the adhesive used in a conventional adhesive bandage. An electromagnetic fiducial element 14 is integrated with the bondable strip 12 and formed with a bottom shell 16 and a top shell 18 clasped together as a housing that partially or fully contains (e.g., envelops, encloses, covers, shrouds, surrounds, conceals, or the like) a low frequency coil drive printed circuit board (PCB) 20. A medically imagable target 24 crosshairs is created with a radiopaque filler that has been compounded with the thermoplastic material used to form the top shell 18. A representation 25 of the target 24 is visibly apparent in medical images captured via x-ray or fluoroscopy. The PCB 20 carries a coin cell battery power source 22, a controller 40, and other electronic circuits to desirably create a controlled magnetic field about an electromagnetic coil assembly 30. The electromagnetic coil assembly 30 includes an electromagnetic coil section 34 and a core 32. The electromagnetic coil assembly 30 is electrically coupled to the PCB 20 via a coil soldering section 36 fixedly coupled to an electromagnetic coil assembly bond pad 38.

In some cases of the method, the method calls out a plurality of electromagnetic fiducial element assemblies 10. In some cases, the method calls out a single electromagnetic fiducial element assembly 10. In the alternative to a bonding means 26 formed as an adhesive, or in addition, one or more electromagnetic fiducial element assemblies 10a can be arranged as in FIG. 6 with a longer flexible substrate 44 formed as belt, which may be regionally bondable (e.g., hook and loop, adhesive, buckle, clasp, or the like), and which may include conductive fibers, wires, or other structures to pass control signals, information, or the like. The method is now described.

Figure 16:
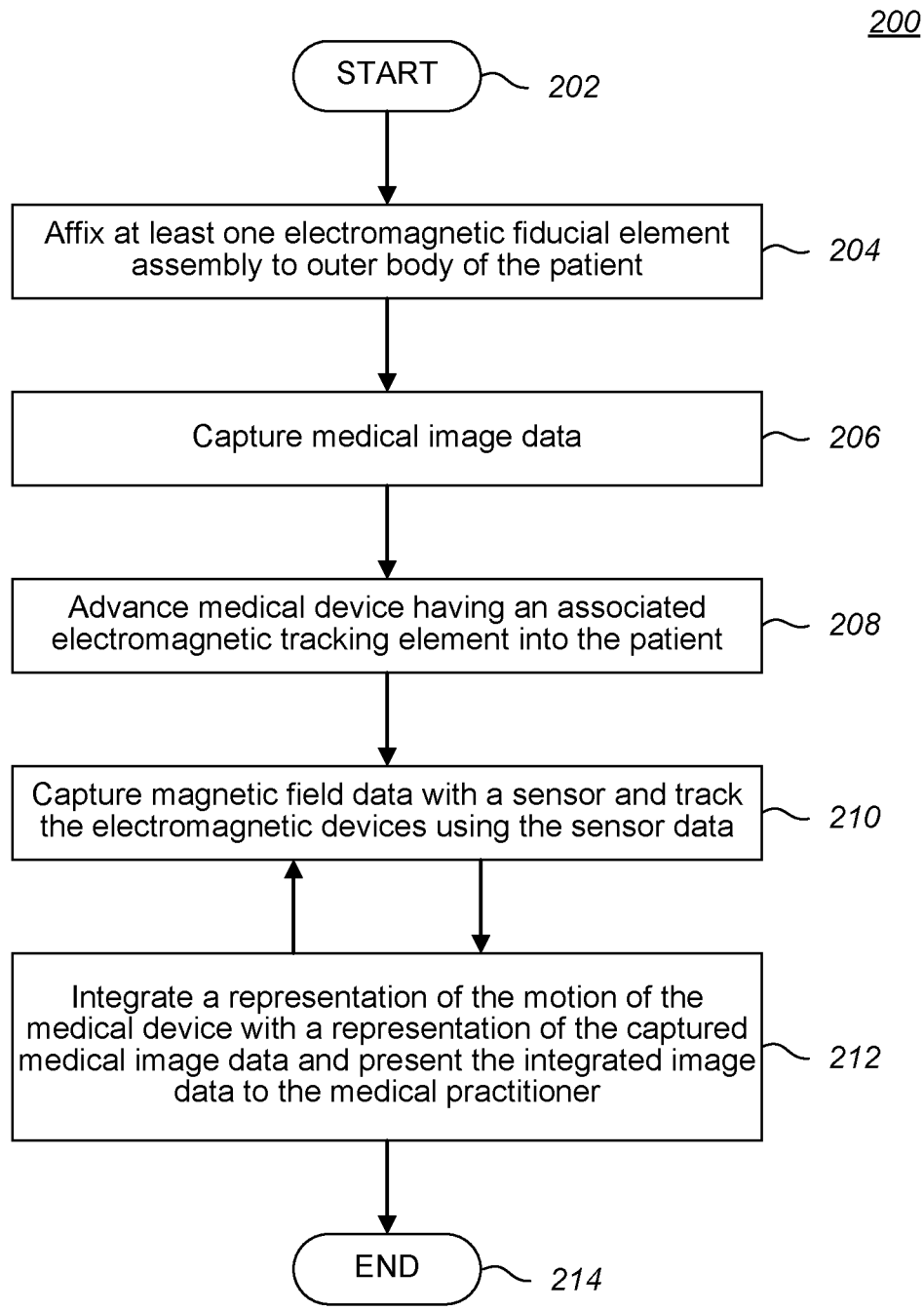
FIG. 16 is a data flow diagram of an electromagnetic fiducial element assisted medical procedure.

FIG. 16 is a data flow diagram 200 of an electromagnetic fiducial element assisted medical procedure. The medical procedure begins at 202.

At 204, a medical practitioner (not shown) is administering the procedure. The medical practitioner places at least one electromagnetic fiducial element assembly 10 on the body of a patient 50. As described, the electromagnetic fiducial element assembly 10 has a flexible substrate and an affixation mechanism that is arranged to removably affix the electromagnetic fiducial element assembly to the outer body 52 of the patient 50. Considering the flexible substrate and affixation mechanism, the electromagnetic fiducial element assembly 10 may resemble or otherwise be formed as a belt, a pendant, a bracelet, a medallion, or some other structure such as a conventional adhesive bandage that also integrates an unconventional extra structure. The unconventional extra structure is realized as a housing 16, 18 coupled to the flexible substrate (e.g., bondable strip 12) that contains a first trackable electromagnetic fiducial element 14. The electromagnetic fiducial element assembly 10 also includes a medically imagable structure 24. The medically imagable structure 24 can be arranged in many ways. For example, the medically imagable structure 24 may be a crosshair, a target, a device identifier, or some other visibly apparent symbol formed from a substance that will be visibly apparent in a medical image 70. If the medical imagery is x-ray imagery, for example, the medically imagable structure 24 can be formed of a metal, a compound, or some other substance that attenuates the x-rays thereby leaving a representation 25 of the medically imagable structure 24 on any captured medical images 70.

Processing falls to 206 where one or more medical images 70 are captured using a first type of medical imaging. The medical imagery may be x-ray, fluoroscopy, magnetic resonance imaging, ultrasound, or some other medical imagery. In some cases, the medical image data is a single image, a set of images, a stream of images (e.g., a video), or some other format of data. A representation 25 of the medically imagable structure 24 is visually apparent in the medical images 70 formed from the medical image data. After the medical image data is captured, the data is stored. The image data is now in the form of a set of stored images that are static. The imaging of the patient using this first type of imaging is terminated. The patient is no longer subject to the effects of the imaging since the imaging procedure has fully terminated. The sequence then advances to 208.

At 208, the medical practitioner has advanced the medical device 60 into the body of the patient 50. Advancing the medical device 60 may include advancing, retracting, rotating, or any other manipulation of the medical device 60 by the medical practitioner. The medical device 60 has an associated electromagnetic coil assembly 30a. A portion of the medical device 60 may be advanced through the mouth of the patient 50 or through another of the patient's orifices. Alternatively, the medical device 60 may be advanced through a surgical incision made by the medical practitioner at some location on the body of the patient 50. The medical device 60 may be advanced, placed, moved, or manipulated in other ways. In the medical procedure now under discussion, the electromagnetic fiducial element 14 of the electromagnetic fiducial element assembly 10 may be referred to as a first trackable electromagnetic element, and the electromagnetic coil assembly 30a of the medical device 60 may be referred to as a second trackable electromagnetic element.

At 210, and in cooperation with processing at 212, magnetic field data is captured with a sensor 64 device, and the first and second trackable electromagnetic elements are tracked. This capture of magnetic data is used to generate an imaging of the trackable electromagnetic element 30 on previously captured medical images, and not a medical imaging of the patient. A second, type of imaging, which is different than the first type of medical imaging, is used, for example, electromagnetic data capture. The device tracking information is used to merge a representation of the motion of the medical device 60 with a representation of the captured medical image data and present the merged image data to the medical practitioner via the user interface 104. Bi-directional data flow arrows between processing at 210 and 212 indicate that the processes are iterative, cooperative, and related.

The sensor 64 device is arranged to capture magnetic field data and track a plurality of trackable electromagnetic elements. The sensor 64 is a magnetic field sensing device operated by the medical practitioner proximal to the body of the patient 50. In some cases, the medical practitioner places the sensor 64 directly in contact with the body of the patient 50. Generally speaking, the medical practitioner will attempt to place the sensor 64 adjacent to the portion of the body where the medical device 60 inside the patient's body is believed to be. The sensor 64 captures signal information from the first and second trackable electromagnetic elements. In this case, the first trackable electromagnetic element (i.e., the electromagnetic fiducial element 14 of the electromagnetic fiducial element assembly 10) is a stable, non-moving electromagnetic element that is used as a reference point. The second trackable electromagnetic element (i.e., the electromagnetic coil assembly 30a of the medical device 60) is a moving electromagnetic element.

In the medical procedure under discussion, a user interface 104 associated with the sensor 64 includes presentation system, which may include one or more of a video display, an audio input/output system, a tactile feedback system, or some other presentation mechanism. The user interface 104 may further include one or more user input interfaces for keyboards, mice, touch screens, buttons, dials, and other like controls. The user interface 104 may be arranged to receive and present output information captured from the sensor 64. Embodiments of the user interface 104 are used to present the medical image 70 and also used to present information representing the position and orientation of the medical device as an overlay onto the medical image 70. Stated differently, by receiving and processing magnetic field information provided by two or more low-frequency electromagnetic apparatuses, a control circuit 102 (FIG. 14) is able to generate image data representing the medical device in one or more previously captured medical images.

Processing in the data flow of FIG. 16 ends at 214.

A medical device (e.g., medical instrument) refers to an instrument, apparatus, constructed element or composition, machine, implement, or similar or related article that can be utilized to diagnose, prevent, treat or manage a disease or other condition(s). The medical devices provided herein may, depending on the device and the embodiment, be implanted within a patient, utilized to deliver a device to a patient, or utilized externally on a patient. In many embodiments the medical devices provided herein are sterile and subject to regulatory requirements relating to their sale and use.

In the present disclosure, the tracking of medical instruments or portions thereof (e.g., electromagnet structures) is performed to an acceptable accuracy. As used in the present disclosure, "acceptable accuracy" is any level of accuracy determined to be acceptable by a medical practitioner performing a respective medical procedure. For example, in the placement of a cardiovascular medical instrument, acceptable accuracy may be within one centimeter (1 cm), within one millimeter (1 mm), within 100 microns, or within some other measurement. In other medical procedures, for example in the placement of a feeding tube (e.g., a percutaneous endoscopic gastrostomy (PEG) tube), the acceptable accuracy may be within five centimeters (5 cm), within two centimeters (2 cm), or within some other measurement. In some cases, acceptable accuracy is determined linearly within two dimensions. In other cases, acceptable accuracy is determined in three dimensions. In some cases, acceptable accuracy includes a time parameter such that information associated with distance and positional tracking of a medical instrument is associated with a measure of time. For example, acceptable accuracy in some cases may include a first position of a medical instrument at a first time and a second position of the medical instrument at a second time. Time parameters, when associated with an acceptable accuracy, may include linear time, rate, rate of change, or any other such time parameter.

Certain words and phrases used in the specification are set forth as follows. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation, such a device may be implemented in hardware, firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

A processor (i.e., a processing unit), as used in the present disclosure, refers to one or more processing units individually, shared, or in a group, having one or more processing cores (e.g., execution units), including central processing units (CPUs), digital signal processors (DSPs), microprocessors, micro controllers, state machines, and the like that execute instructions. In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files.

The files may include functions, services, libraries, and the like. The files may include one or more computer programs or may be part of a larger computer program. Alternatively, or in addition, each file may include data or other computational support material useful to carry out the computing functions of the systems, methods, and apparatus described in the present disclosure. Some or all of the stored contents of a memory may include software instructions executable by a processing device to carry out one or more particular acts.

In the present disclosure, certain features may be implemented with one or more computing devices. For brevity, the computing devices are not shown in detail in the present figures because one of skill in the art will recognize that a computing device includes a plurality of computing circuits such as at least one processor communicatively coupled to at least one memory and arranged to execute instructions that are stored in the memory to implement various features of a system for detecting the position of a medical instrument within the body of a patient. The control circuit 102 (FIG. 14), for example, may include one or more computing devices that direct the generation of excitation signals, that direct the detection and capture of magnetic field signals, that produce position information, that present the position information through an input/output device, and that perform other tasks. Resources of such computing devices may be shared to implement one or more of the features, or the resources of such computing devices may be dedicated to implementing certain ones of the features. Resources of such computing devices are in some cases located exclusively in the control circuit 102. In other cases, however, portions of computing resources may be located in a sensor, an input/output device, a medical device, a handheld device, a network-connected remote device, or some other device.

The terms "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis. An example of an activity that is not real-time is one that occurs over an extended period of time (e.g., hours or days) or that occurs based on intervention or direction by a person or other activity, such as each magnetic sense measurement occurring at the press of a button. In the foregoing description, certain specific details are set forth to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments. Unless the context requires otherwise, throughout the specification and claims which follow, the word "comprise" and variations thereof, such as "comprises" and "comprising," are to be construed in an open, inclusive sense, e.g., "including, but not limited to."

In the absence of any specific clarification related to its express use in a particular context, where the terms "substantial" or "about" in any grammatical form are used as modifiers in the present disclosure and any appended claims (e.g., to modify a structure, a dimension, a measurement, or some other characteristic), it is understood that the characteristic may vary by up to 30 percent. For example, a control circuit may be described as producing an excitation between about 200 Hz and about 500 Hz. In these cases, an excitation signal vary in frequency up to 30 percent. Accordingly, an excitation signal that is between 50 Hz and 650 Hz is between about 200 Hz and about 500 Hz. Conversely, excitation signals that are less than 50 Hz or greater than 650 Hz are not between about 200 Hz and 500 Hz.

As another example, a fiducial element assembly having a particular linear dimension of "between about 1.5 inches and about 5.0 inches includes such devices in which the linear dimension varies by up to 30 percent, Accordingly, the particular linear dimension of the fiducial element assembly may be between 0.0 inches and 6.5 inches (i.e., less than or equal to 6.5 inches).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

The headings and Abstract of the Disclosure provided herein are for convenience only and do not limit or interpret the scope or meaning of the embodiments.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An electromagnetic fiducial element assembly, comprising:
    a flexible substrate;
    an affixation mechanism arranged to removably affix the flexible substrate to a patient's body;
    an electromagnetic fiducial element, in operation, transmitting a low-frequency magnetic dipole field that alternates in polarity, the electromagnetic fiducial element having a first surface and a second surface opposite the first surface, the second surface of the electromagnetic fiducial element facing the flexible substrate, the electromagnetic fiducial element including:
    a housing coupled to the flexible substrate;
    a trackable electromagnetic element;
    a printed circuit board having a first surface and a second surface opposite the first surface, the printed circuit board extending in a first direction;
    an electromagnetic coil assembly mounted on the second surface of the printed circuit board, the electromagnetic coil assembly longitudinally extending in the first direction; and
    a medically imagable structure on the first surface of the electromagnetic fiducial element, the medically imagable structure arranged to form a visually apparent representation of the medically imagable structure in a stored medical image of a portion of the patient's body, said stored medical image having been previously captured when the electromagnetic fiducial element is affixed to the patient's body.

2. The electromagnetic fiducial element assembly of claim 1, wherein the medically imagable structure is formed from a radiopaque material and wherein the medical image is an x-ray image or a fluoroscopy image.

3. The electromagnetic fiducial element assembly of claim 2, wherein the medically imagable structure is shaped as a crosshair.

4. The electromagnetic fiducial element assembly of claim 1, wherein the affixation mechanism is an adhesive.

5. The electromagnetic fiducial element assembly of claim 1, comprising:
    a second trackable electromagnetic element.

6. The electromagnetic fiducial element assembly of claim 1, wherein the electromagnetic coil assembly includes:
    a core;
    an electromagnetic coil section; and
    a first and second coil soldering contact sections, the electromagnetic coil section between the first and second coil soldering contact sections.

7. The electromagnetic fiducial element assembly of claim 6, comprising:
    an electromagnetic coil assembly bond pad contact on the second surface of the printed circuit board, the electromagnetic coil assembly bond pad contact coupled to at least one of the first and second coil soldering contact sections.

8. The electromagnetic fiducial element assembly of claim 1, wherein the housing includes:

a top shell; and
a bottom shell,
wherein the printed circuit board is housed in the bottom shell,
wherein the top shell covers over the bottom shell, and
wherein the medically imagable structure is on a surface of the top shell.

9. The electromagnetic fiducial element assembly of claim 8, comprising:
a battery arranged on a first section of the printed circuit board; and
a controller arranged on a second section of the printed circuit board, the second section and the first section being adjacent to each other.

10. The electromagnetic fiducial element assembly of claim 6, comprising:
a battery arranged on a first section of the printed circuit board;
a controller arranged on a second section of the printed circuit board, the second section and the first section being adjacent to each other.

11. The electromagnetic fiducial element assembly of claim 9, wherein a portion of the battery protrudes from the surface of the top shell.

12. The electromagnetic fiducial element assembly of claim 10, wherein the medical imagable structure is between the first and second section, and
wherein a portion of the medical imagable structure overlaps with the protruded portion of the battery.

13. The electromagnetic fiducial element assembly of claim 1, wherein the flexible substrate includes a flexible, bondable strip.

\* \* \* \* \*

UNITED STATES PATENT AND TRADEMARK OFFICE
CERTIFICATE OF CORRECTION

PATENT NO. : 11,426,133 B2
APPLICATION NO. : 16/352778
DATED : August 30, 2022
INVENTOR(S) : Curtis S. King It is certified that error appears in the above-identified patent and that said Letters Patent is hereby corrected as shown below:

In the Claims

Column 24, Claim 1, Line 31:
"a medically imagable structure" should read: --a medically imageable structure--.

Column 24, Claim 1, Line 33:
"imagable structure" should read: --imageable structure--.

Column 24, Claim 1, Line 34:
"the medically imagable structure" should read: --the medically imageable structure--.

Column 24, Claim 2, Line 40:
"the medically imagable structure" should read: --the medically imageable structure--.

Column 24, Claim 3, Line 44:
"the medically imagable structure" should read: --the medically imageable structure--.

Column 25, Claim 12, Line 26:
"the medical imagable structure" should read: --the medical imageable structure--.

Signed and Sealed this
Thirteenth Day of August, 2024

Katherine Kelly Vidal
*Director of the United States Patent and Trademark Office*